United States Patent
Tada et al.

(10) Patent No.: US 10,588,913 B2
(45) Date of Patent: Mar. 17, 2020

(54) AQUEOUS SUSPENSION AGENT CONTAINING GLUCOCORTICOSTEROID NANOPARTICLES

(71) Applicant: ACTIVUS PHARMA CO., LTD., Funabashi-shi, Chiba (JP)

(72) Inventors: Takahiro Tada, Funabashi (JP); Kazuhiro Kagami, Funabashi (JP); Kenta Kikuchi, Funabashi (JP)

(73) Assignee: Activus Pharma Co., Ltd., Funabashi-shi, Chiba (JP)

( * ) Notice: Subject to any disclaimer, the term of this patent is extended or adjusted under 35 U.S.C. 154(b) by 0 days.

(21) Appl. No.: 15/571,986

(22) PCT Filed: May 9, 2016

(86) PCT No.: PCT/JP2016/063752
§ 371 (c)(1),
(2) Date: Nov. 6, 2017

(87) PCT Pub. No.: WO2016/181935
PCT Pub. Date: Nov. 17, 2016

(65) Prior Publication Data
US 2018/0117064 A1 May 3, 2018

(30) Foreign Application Priority Data
May 8, 2015 (JP) .................. 2015-095610

(51) Int. Cl.
| | |
|---|---|
| *A61K 31/573* | (2006.01) |
| *A61K 31/58* | (2006.01) |
| *A61K 31/57* | (2006.01) |
| *A61K 47/10* | (2017.01) |
| *A61K 9/10* | (2006.01) |
| *A61K 47/34* | (2017.01) |
| *A61K 47/32* | (2006.01) |
| *A61K 47/24* | (2006.01) |
| *A61K 47/12* | (2006.01) |
| *A61K 47/38* | (2006.01) |
| *A61P 31/04* | (2006.01) |
| *A61P 29/00* | (2006.01) |

(52) U.S. Cl.
CPC .............. *A61K 31/573* (2013.01); *A61K 9/10* (2013.01); *A61K 31/57* (2013.01); *A61K 31/58* (2013.01); *A61K 47/10* (2013.01); *A61K 47/12* (2013.01); *A61K 47/24* (2013.01); *A61K 47/32* (2013.01); *A61K 47/34* (2013.01); *A61K 47/38* (2013.01); *A61P 29/00* (2018.01); *A61P 31/04* (2018.01)

(58) Field of Classification Search
CPC ...... A61K 31/573; A61K 31/58; A61K 31/57; A61K 47/10; A61K 9/10; A61K 47/34; A61K 47/32; A61K 47/24; A61K 47/12; A61K 47/38; A61P 29/00; A61P 31/04
See application file for complete search history.

(56) References Cited

U.S. PATENT DOCUMENTS

| | | |
|---|---|---|
| 6,132,751 A | 10/2000 | Suzuki et al. |
| 6,274,634 B1 | 8/2001 | Yasueda et al. |
| 8,226,983 B2 | 7/2012 | Hirokawa et al. |
| 9,278,071 B2 | 3/2016 | Tada et al. |
| 9,782,484 B2 | 10/2017 | Hirokawa et al. |
| 2007/0178051 A1 | 8/2007 | Pruitt et al. |
| 2010/0016597 A1 | 1/2010 | Hirokawa et al. |
| 2011/0008453 A1 | 1/2011 | Shaw et al. |
| 2011/0165259 A1 | 7/2011 | Hirokawa et al. |
| 2012/0237768 A1 | 9/2012 | Hirokawa et al. |
| 2014/0038931 A1 | 2/2014 | Hirokawa et al. |
| 2014/0328917 A1 | 11/2014 | Tada et al. |
| 2015/0258120 A1 | 9/2015 | Zarnitsyn et al. |

FOREIGN PATENT DOCUMENTS

| | | | |
|---|---|---|---|
| CN | 101636150 A | | 1/2010 |
| CN | 102149410 A | | 8/2011 |
| CN | 104203217 A | | 12/2014 |
| EP | 2 848 243 A1 | | 3/2015 |
| JP | 2003-055262 A | | 2/2003 |
| JP | 2005-536512 A | | 12/2005 |
| WO | WO 96/25919 A1 | | 8/1996 |
| WO | WO 97/05882 A1 | | 2/1997 |
| WO | WO 00/25746 | * | 5/2000 |

(Continued)

OTHER PUBLICATIONS

International Search Report for International Application No. PCT/JP2016/063752, dated Jul. 19, 2016.
Written Opinion of the International Searching Authority for International Application No. PCT/JP2016/063752, dated Jul. 19, 2016.
Ali et al., "Hydrocortisone nanosuspensions for ophthalmic delivery: A comparative study between microfluidic nanoprecipitation and wet milling," *Journal of Controlled Release*, vol. 149, pp. 175-181 (2011).

(Continued)

*Primary Examiner* — Sahar Javanmard
(74) *Attorney, Agent, or Firm* — Knobbe, Martens, Olson & Bear, LLP

(57) ABSTRACT

An aqueous suspension containing as an active component a glucocorticosteroid compound is described. The aqueous suspension contains nanoparticles of a glucocorticosteroid compound and a dispersion stabilizer. The nanoparticles have a mean particle diameter of 300 nm or less and a D90 particle diameter of 450 nm or less. The pharmaceutical compositions containing the aqueous suspension are for parenteral administrations, injections, eye drops or ear drops. More specifically the aqueous suspensions containing glucocorticosteroid nanoparticles are used as an eye drop for treating or preventing inflammatory diseases of the eye or an ear drop for treating or preventing inflammatory diseases of the ear.

16 Claims, 7 Drawing Sheets

(56) References Cited

FOREIGN PATENT DOCUMENTS

| WO | WO 2004/006959 A1 | 1/2004 |
|----|-------------------|--------|
| WO | WO 2007/089490 A1 | 8/2007 |
| WO | WO 2009/139924 A1 | 11/2009 |
| WO | WO 2008/126797 A1 | 7/2010 |
| WO | WO 2010/032434 A1 | 2/2012 |
| WO | WO 2014/074823 A1 | 5/2014 |

OTHER PUBLICATIONS

Donnenfeld, "Difluprednate for the prevention of ocular inflammation postsurgery: an update," *Clinical Opthalmology*, vol. 5, pp. 811-816 (2011).

Patel et al., "Topical delivery of clobetasol propionate loaded microemulsion based gel for effective treatment of vitiligo: Ex vivo permeation and skin irritation studies," *Colloids and Surfaces B: Biointerfaces*, vol. 102, pp. 86-94 (2013).

Yang et al., "Fluticasone and Budesonide Nanosuspensions for Pulmonary Delivery: Preparation, Characterization, and Pharmacokinetic Studies," *Journal of Pharmaceutical Sciences*, vol. 97(11), pp. 4869-4878 (Nov. 2008).

Extended European Search Report received in connection with European Patent Application No. 16792660.9 dated Dec. 3, 2018.

Search Report in Chinese Patent Application No. 201680026845.5 dated Aug. 13, 2019.

Search Report in Taiwan Patent Application No. 105114243 dated Sep. 11, 2019.

Office Action and Search Report in Russian Patent Application No. 2017142694 dated Nov. 11, 2019.

\* cited by examiner

[Figure 1]
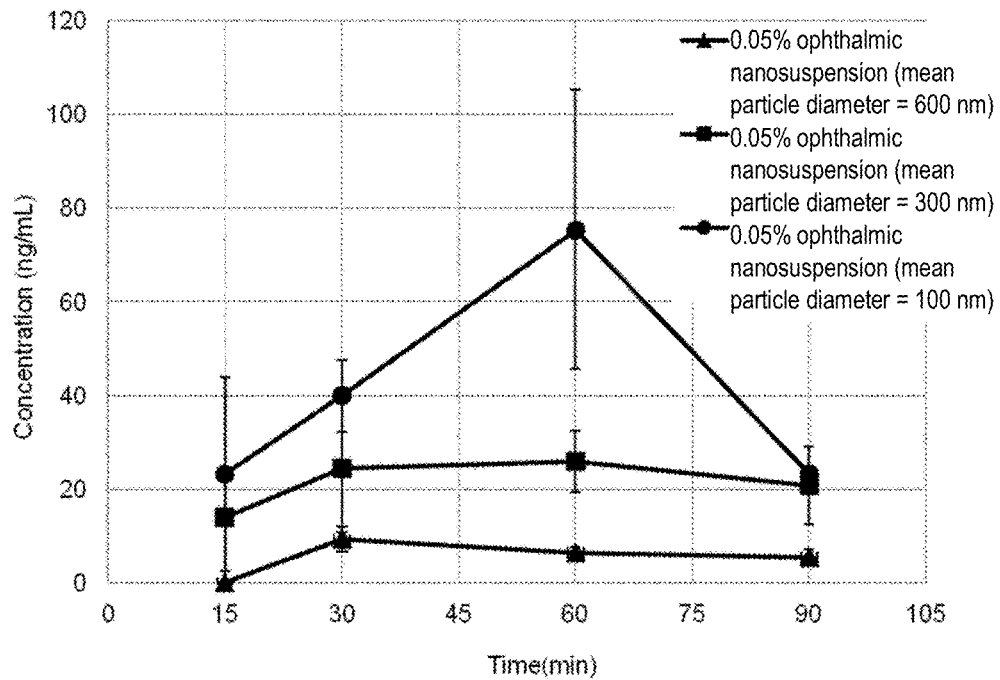
[Figure 2]
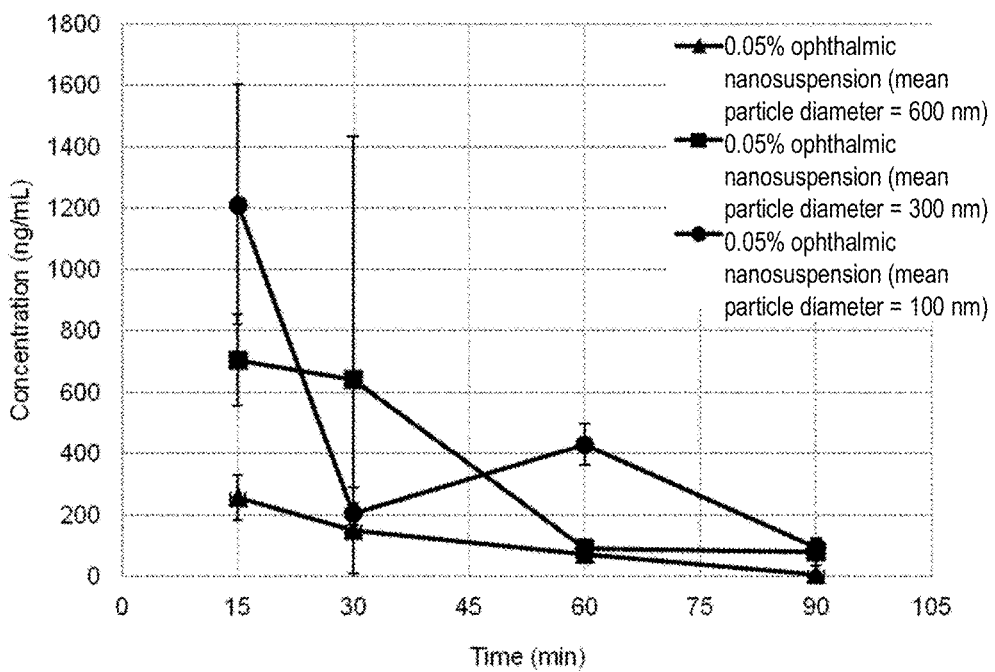

[Figure 3]
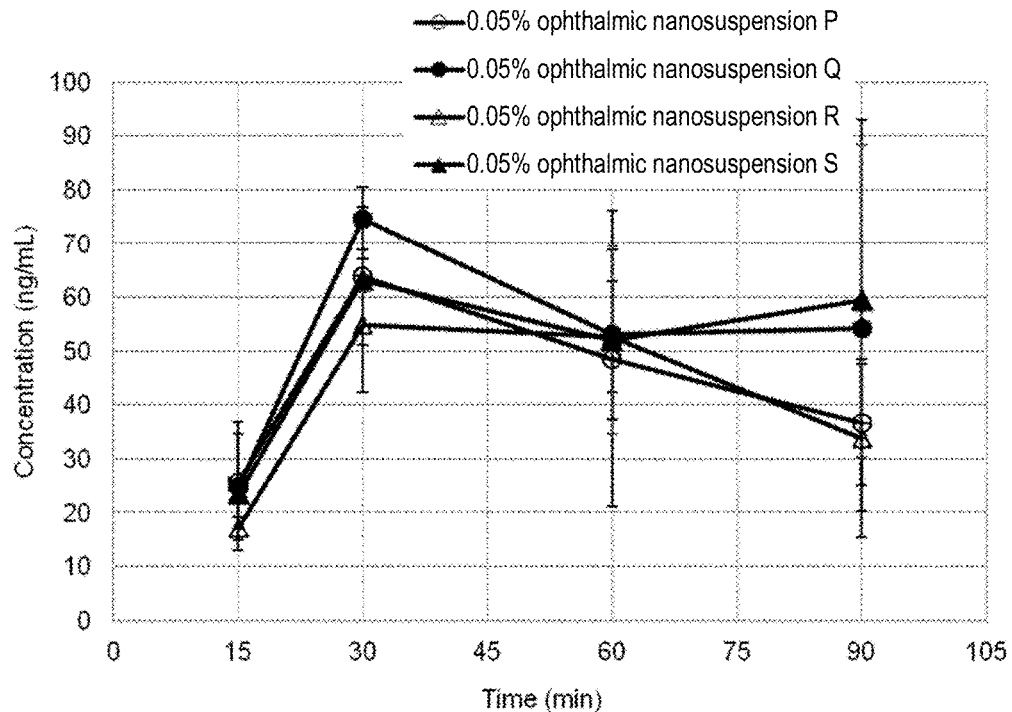
[Figure 4]
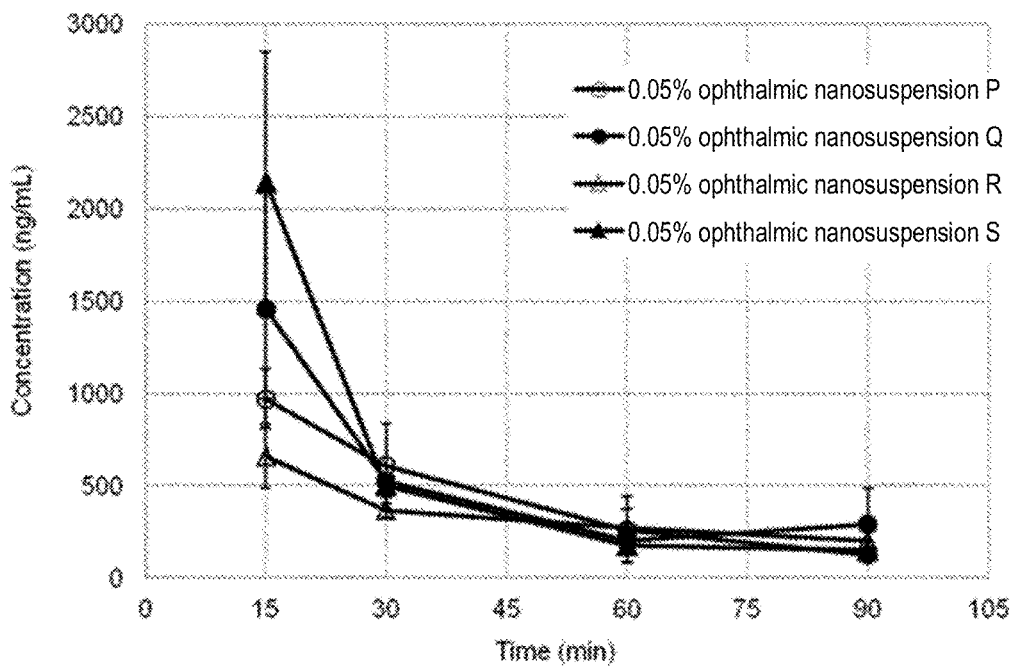

[Figure 5]
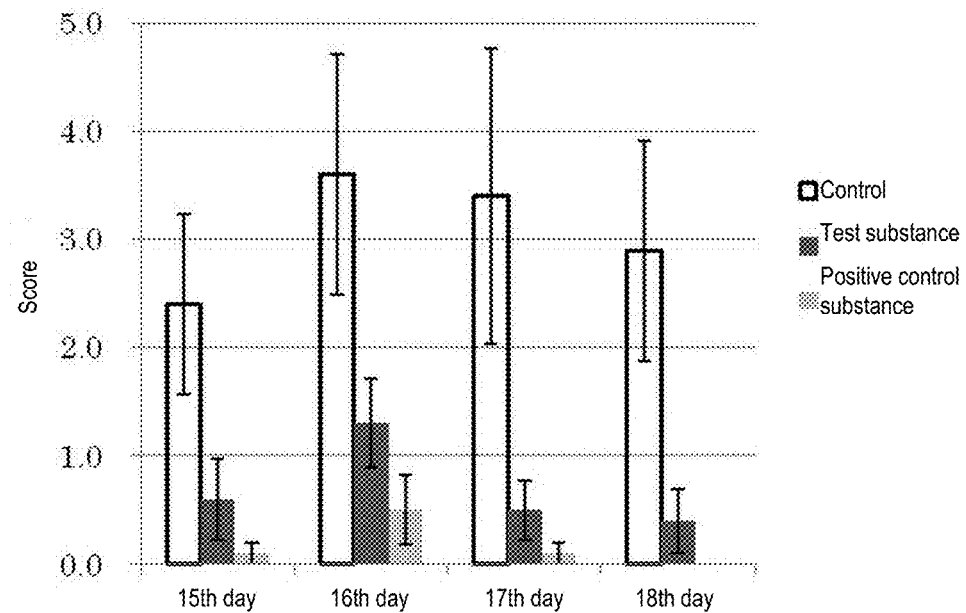
[Figure 6]
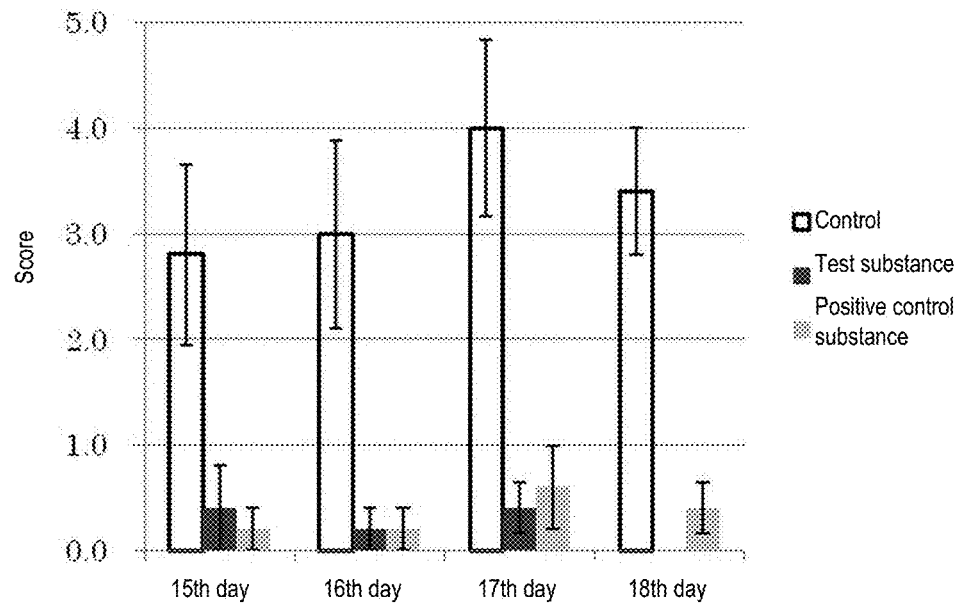

[Figure 7]
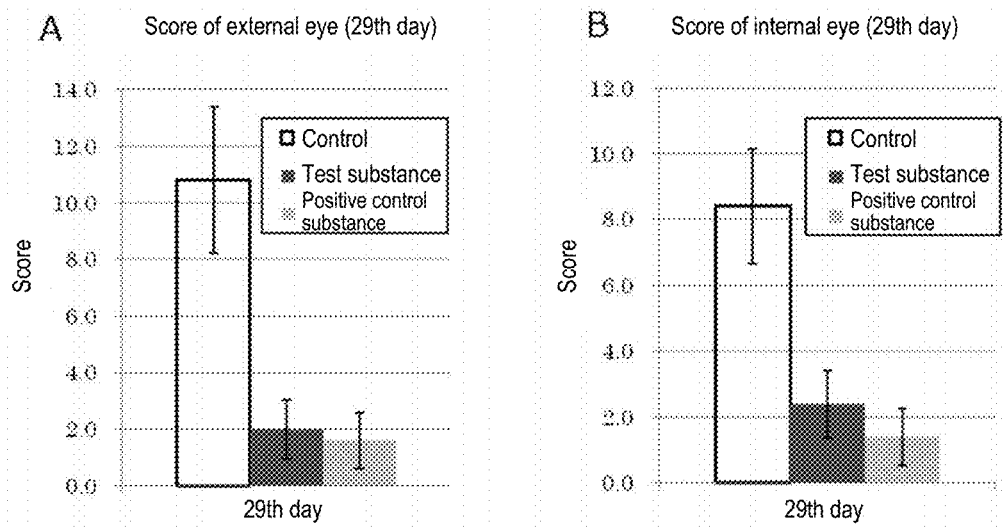
[Figure 8]
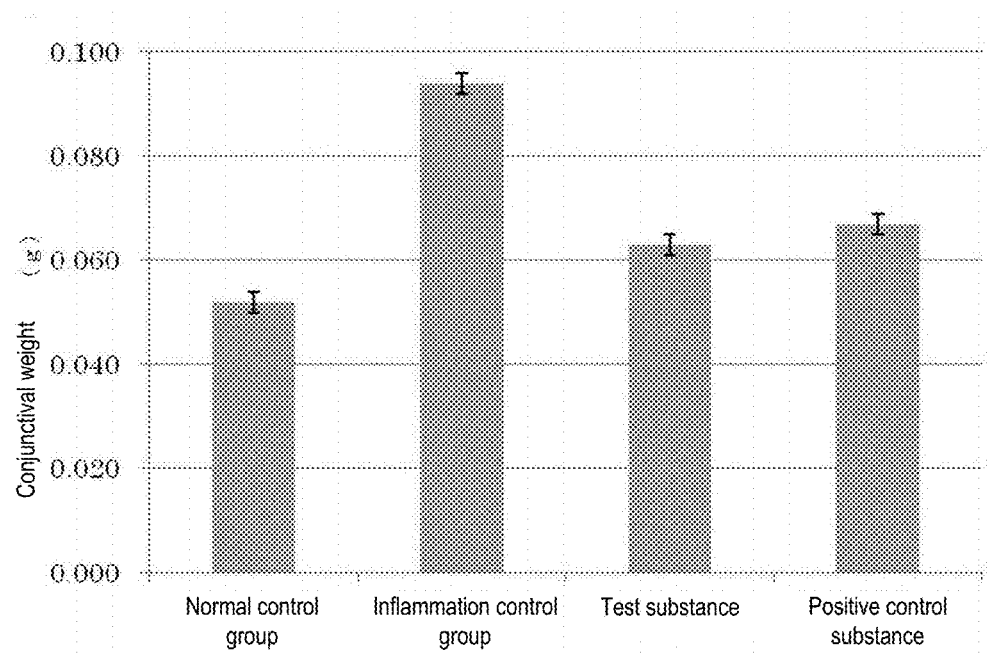

[Figure 9]
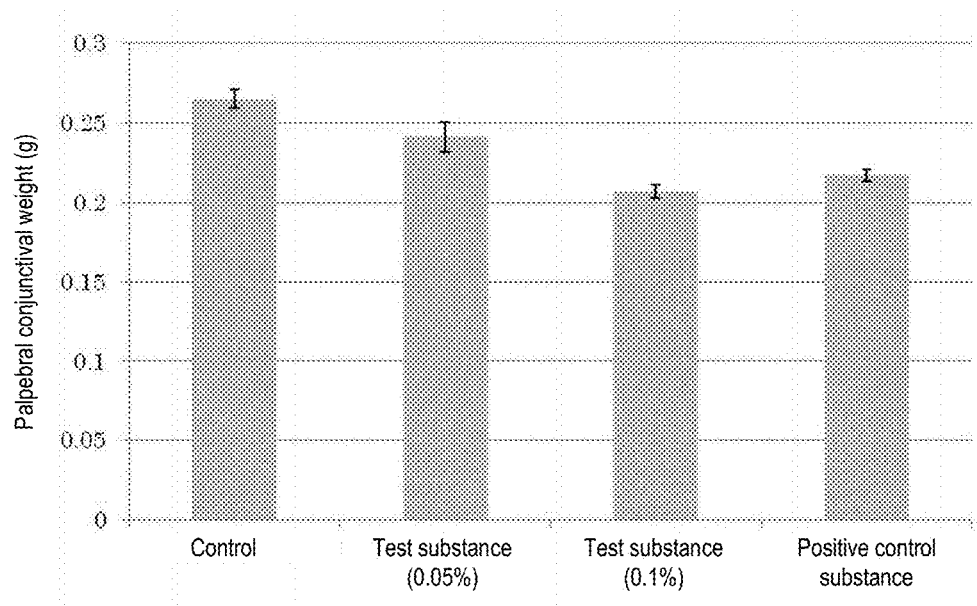
[Figure 10]
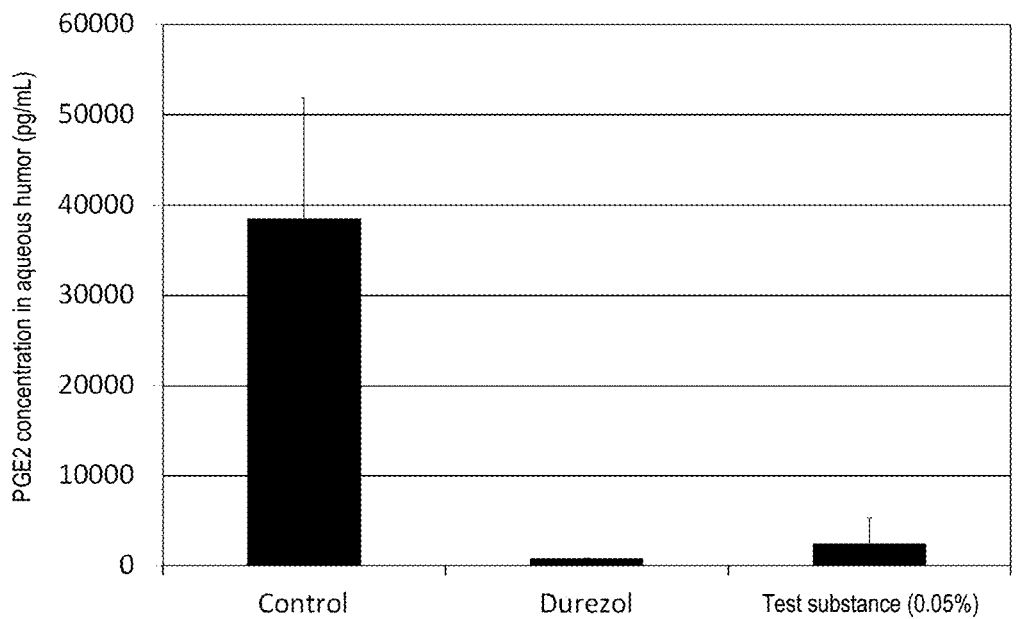

[Figure 11]
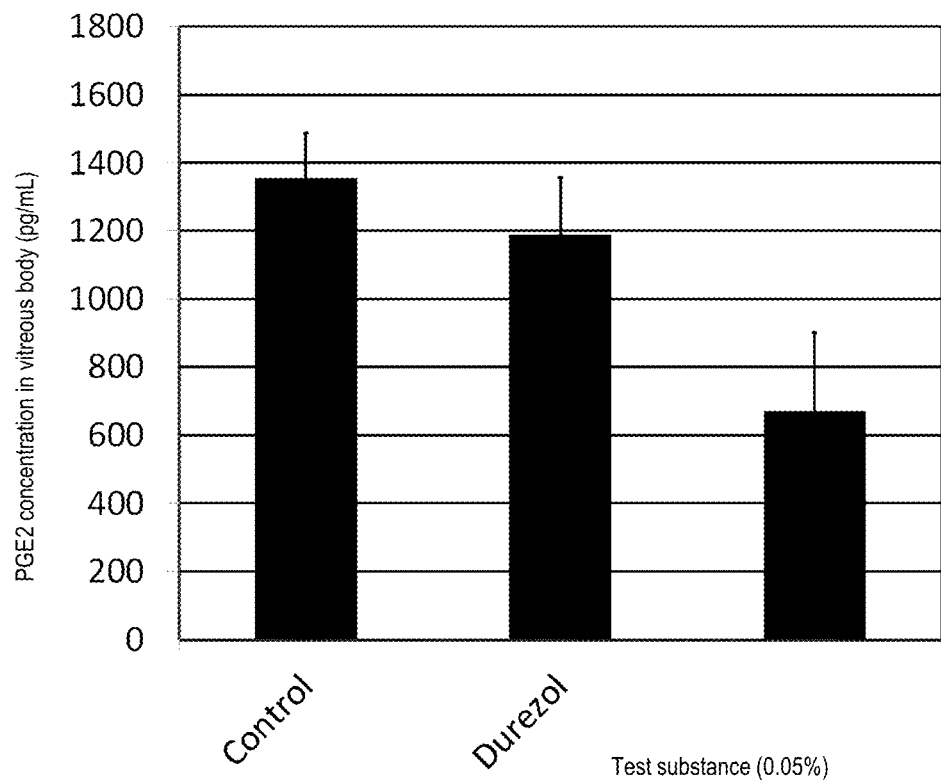
[Figure 12]
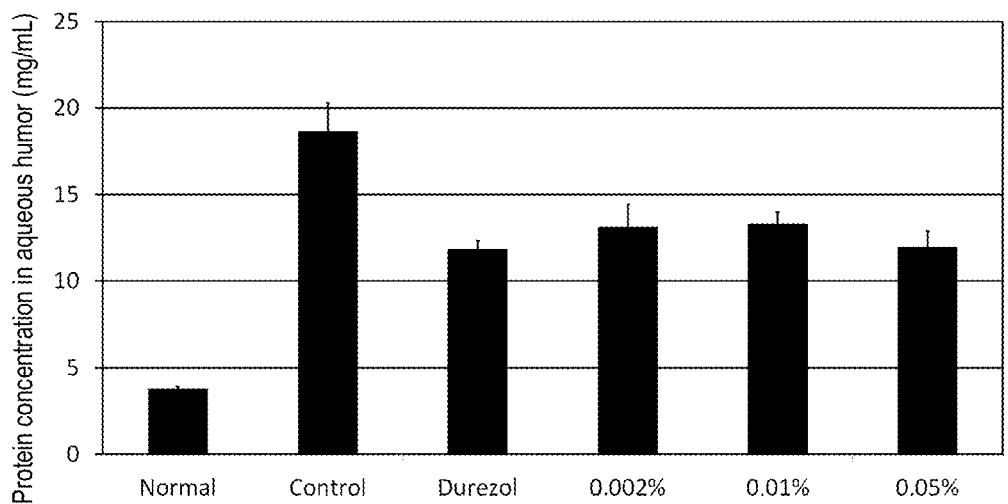

[Figure 13]
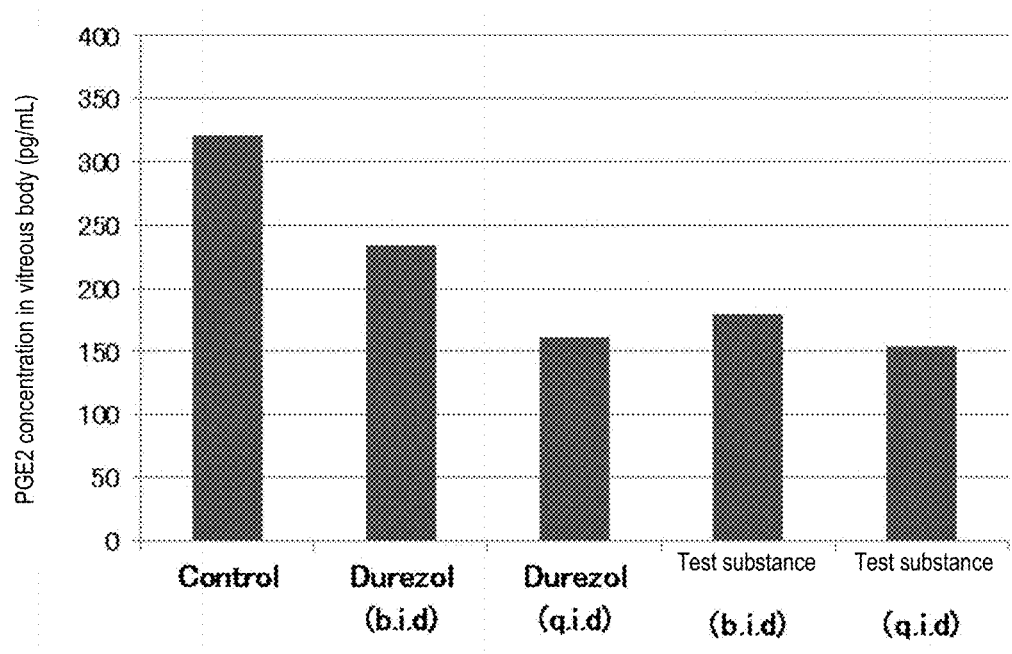

AQUEOUS SUSPENSION AGENT CONTAINING GLUCOCORTICOSTEROID NANOPARTICLES

CROSS-REFERENCE

This application claims the priority to Japanese Patent Application No. 2015-095610, filed on May 8, 2015, and all disclosures of which are incorporated herein by reference in its entirety. All of the contents disclosed in the cited patents, patent applications, and literatures are incorporated herein by reference in their entireties.

TECHNICAL FIELD

The present invention relates to an aqueous suspension containing glucocorticosteroid nanoparticles and the use thereof.

BACKGROUND ART

Glucocorticosteroids are hydrophobic and have been provided in the form of aqueous suspensions. However, the aqueous suspension of a glucocorticosteroid compound have a problem that the contained steroid particles precipitate as time advances, and thus a patient needs to shake a container before use to disperse an active component homogeneously in the liquid phase. Even in case that a patient shook a container before use without fail, the particles in the suspension easily agglomerate to form cluster, thereby the particle diameter of the drug increases and the uniformity is lost. Such a ununiform dispersion caused a loss in an administration dose that is predetermined and consequent insufficient suppression of inflammation and pains.

In order to solve such a problem caused by the steroid, emulsion preparations have been proposed (Patent Literature 1, Non Patent Literatures 1, 2) as one of the methods. For example, Difluprednate O/W emulsion preparation (Durezol (Registered trademark): a 0.05% difluprednate preparation) has been confirmed to be stably applied to affected area with a uniform drug regardless of storage conditions or shaking before use.

However, the O/W emulsion preparation requires to use an oil solvent, which causes a problem of irritating effects such as uncomfortable sensations or congestion. Thus, it has been required to prepare glucocorticosteroid aqueous preparations without using oil solvent that can maintain the uniformity.

Modification of structure which gives hydrophilicity to the compound, such as Dexamethasone sodium phosphate, has been attempted to dissolve the compound in water. However, the water dissolved preparations could contain limited concentration of an active component due to the poor solubility.

As alternative aqueous solution containing a hardly soluble drug, nanosuspensions which contains nano-sized particles of an active component in an aqueous suspension have been proposed. It has been known that the particle diameter as small as nanometer substantially extends specific surface area in the nanosuspensions, and this enables faster maximization of the serum level of the component due to its increased solubility, variety of administration forms, and higher amount of an active component to be contained. As the nanosuspension of a glucocorticosteroid compound, it has been disclosed that the aqueous suspension containing fluticasone (D90 0.4 μm) and budesonide (D90 0.4 μm) produced by a wet mill using glass beads maintained the uniformity, crystal structure, and particle diameter after five weeks preservation at 4° C. (Non Patent Literature 3). Another approach for forming nanoparticles as bottom-up approach has been reported that precipitates hydrocortisone, a glucocorticosteroid compound, so as to generate nanoparticles having a mean diameter of about 300 nm, which is prepared as an aqueous suspension (Non Patent Literature 4). However, they also reported that the top-down approach (milling) is more advantageous in both intraocular pressure elevation and stability. Another nanosuspension containing a corticosteroid (specifically, mometasone furoate) mainly used for transnasal administration has been disclosed which contains corticosteroid having a D50 of 50 to 500 nm, a hydrophilic polymer, a wetting agent, and a complexing agent (Patent Literature 2). Additionally, an autoclave-sterilizable aqueous suspension of a glucocorticosteroid compound has been reported (Patent Literature 3).

CITATION LIST

Patent Literature

[Patent Literature 1] International Publication No. WO 97/05882
[Patent Literature 2] U.S. Unexamined Patent Application Publication No. 2011/0008453
[Patent Literature 3] International Publication No. WO 2007/089490

Non Patent Literature

[Non Patent Literature 1] Eric D Donnenfeld, Clinical Opthalmology (2011) 5:811-816
[Non Patent Literature 2] Hetal K. Patel et al., Colloids and Surfaces: Biointerfaces (2013) 102:86-94
[Non Patent Literature 3] Jerry Z. Yang et al., Journal of Pharmaceutical Sciences (2008) 97 (11):4869-4878
[Non Patent Literature 4] Hany S. M. Ali et al., Journal of Controlled Release (2011) 149:175-181

SUMMARY OF INVENTION

Technical Problem

Despite extensive studies on aqueous solutions containing such hardly soluble agents, it is still difficult to practically use aqueous suspensions such as injections, eye drops and ear drops containing a glucocorticosteroid compound such as clobetasol propionate. It has thus been expected to develop aqueous suspensions for injections and for topical administrations, specifically eye drops and ear drops, containing a glucocorticosteroid compound as the active component with good temporal stability and dispersion stability.

Accordingly, in one embodiment, the present invention is aimed to provide an aqueous suspension containing as an active component a glucocorticosteroid compound, which has good temporal stability and dispersion stability. More specifically, the present invention is aimed to provide aqueous pharmaceutical compositions such as injections, eye drops, ear drops, nose drops, and/or inhalers containing a glucocorticosteroid compound as the active component, which has good transparency, dispersibility, and storage stability. The further object of the invention is to provide an eye drop containing a glucocorticosteroid compound as an active component, which is high retention in the cornea and good transferability into the aqueous humor. The present invention is also objected to provide an aqueous suspension or an aqueous pharmaceutical composition containing clobetasol propionate, a glucocorticosteroid compound, as the active component.

Solution to Problems

The inventors conducted extensive studies and found that the aqueous suspension containing nanoparticles of a glucocorticosteroid compound and, if necessary, a dispersion stabilizer, a surfactant, an agglomeration inhibitor and/or a viscosity modifier is excellent in transparency, (long term) dispersibility, storage stability, retention in the cornea, and transferability into the aqueous humor, and thus is useful for aqueous pharmaceutical composition. The inventors found that the aqueous suspension containing nanoparticles of a glucocorticosteroid compound and, if necessary, a dispersion stabilizer, a surfactant, an agglomeration inhibitor and/or a viscosity modifier exceptionally achieves good transparency, (long term) dispersibility and storage stability without containing an organic compound that causes irritating effects such as uncomfortable sensations or congestion. With these findings, the inventors have accomplished the highly effective anti-inflammatory aqueous preparation containing a glucocorticosteroid compound which can stably provide a uniform drug to an affected site with less irritation.

The present invention more specifically relates to the followings:
(1) An aqueous suspension containing nanoparticles of a glucocorticosteroid compound.
(2) The aqueous suspension of (1), wherein a mean particle diameter of the nanoparticles is 300 nm or less and a D90 particle diameter of the nanoparticles is 450 nm or less.
(3) The aqueous suspension of (1) or (2), wherein the nanoparticles are produced by mixing a glucocorticosteroid compound, a physiologically acceptable salt, a physiologically acceptable polyol, and a surface modifier.
(4) The aqueous suspension of any one of (1) to (3), wherein the glucocorticosteroid compound is one or more substances selected from clobetasol propionate, diflorasone diacetate, dexamethasone propionate, difluprednate, mometasone furoate, diflucortolone valerate, betamethasone butyrate propionate, fluocinonide, hydrocortisone butyrate propionate, beclomethasone dipropionate, deprodone propionate, betamethasone valerate, dexamethasone valerate, prednisolone valerate acetate, fluocinolone acetonide, hydrocortisone butyrate, clobetasone butyrate, alclometasone dipropionate, triamcinolone acetonide, flumethasone pivalate, prednisolone, and hydrocortisone.
(5) The aqueous suspension of any one of (1) to (4), further containing a dispersion stabilizer.
(6) The aqueous suspension of (5), wherein the dispersion stabilizer is polyoxyethylene polyoxypropylene glycol and/or polyvinyl alcohol.
(7) The aqueous suspension of any one of (1) to (6), further containing a viscosity modifier.
(8) The aqueous suspension of (7), wherein the viscosity modifier is one or more substances selected from methylcellulose, hydroxypropylmethylcellulose and polyvinylalcohol.
(9) The aqueous suspension of (7) or (8), containing 1 to 10 mg/mL of the viscosity modifier.
(10) A pharmaceutical composition containing the aqueous suspension of any one of (1) to (9).
(11) The pharmaceutical composition of (10), which is for parenteral administration.
(12) The pharmaceutical composition of (11), which is for an injection or for a topical preparation.
(13) The pharmaceutical composition of (12), which is for a topical preparation for an eye, an ear, a nose or a lung.
(14) The pharmaceutical composition of (13), which is an eye drop, an ear drop, a nose drop, or an inhaler.
(15) The pharmaceutical composition of any one of (10) to (14), which is a therapeutic agent or a preventive agent for an inflammatory or infectious disease.
(16) The pharmaceutical composition of (15), wherein the inflammatory or infectious disease is a systemic inflammatory or infectious disease.
(17) The pharmaceutical composition of (15), wherein the inflammatory or infectious disease is a topical inflammatory or infectious disease.
(18) The pharmaceutical composition of (17), wherein the topical area is one or more tissues or organs selected from eyes, ears, nose (upper respiratory tract), and lungs (lower respiratory tract).
(19) A kit for preparing the pharmaceutical composition of any one of (10) to (18), comprising nanoparticles of a glucocorticosteroid compound.
(20) A method for manufacturing the pharmaceutical composition of any one of (10) to (18), comprising mixing a glucocorticosteroid compound, a physiologically acceptable salt, a physiologically acceptable polyol and/or water, and a dispersion stabilizer.
(21) The method for manufacturing of (20), comprising mixing a glucocorticosteroid compound, a physiologically acceptable salt, glycerin, anhydrous citric acid, and hydrogenated soybean lecithin.

Particularly, the inventors found that nanoparticles of a glucocorticosteroid compound have excellent transferability into the aqueous humor and an good anti-inflammatory action, when the nanoparticles have a mean particle diameter (hereinafter referred to as "Dv") of 300 nm or less and a 90% diameter (hereinafter referred to as "D90") of 450 nm or less (preferably, a Dv of 250 nm or less and a D90 of 300 nm or less, or a Dv of 200 nm or less and a D90 of 250 nm or less). Employing such nanoparticles, the solubility of the glucocorticosteroid compound is expected to become higher, which increases the bioavailability and reduces the administration dose. The mean particle diameter can be measured as intensity distribution mean particle diameter, volume distribution mean particle diameter, and number distribution mean particle diameter. The Dv herein preferably represents the intensity distribution mean particle diameter.

The present invention thus relates to, in one embodiment, the aqueous suspension containing nanoparticles of a glucocorticosteroid compound, and preferably to the aqueous suspension wherein the nanoparticles has a Dv of 300 nm or less and a D90 of 450 nm or less. The aqueous suspension contains, for example, nanoparticles of a glucocorticosteroid compound produced by mixing a glucocorticosteroid compound, a physiologically acceptable salt, a physiologically acceptable polyol and/or water and a dispersion stabilizer. The aqueous suspension more preferably contains nanoparticles of a glucocorticosteroid compound produced by mixing a glucocorticosteroid compound, a physiologically acceptable salt, glycerin, anhydrous citric acid and hydrogenated soybean lecithin.

The inventors additionally found that the aqueous suspension containing nanoparticles of a glucocorticosteroid compound exhibits good long-term transparency, dispersibility, and storage stability, containing with polyoxyethylene polyoxypropylene glycols (hereinafter referred to as "POE-POP glycol") and/or polyvinyl alcohols (hereinafter referred to as "PVA") as a dispersion stabilizer, and/or containing with hydroxypropyl methylcellulose and/or methyl cellulose as a thickener.

The present invention thus relates to, in one embodiment, the aqueous suspension containing nanoparticles of a glucocorticosteroid compound having a Dv of 300 nm or less and a D90 of 450 nm or less (preferably, a Dv is 250 nm or less and a D90 is 300 nm or less, or a Dv is 200 nm or less and a D90 is 250 nm or less). The present invention relates to, in another embodiment, the aqueous pharmaceutical composition containing nanoparticles of a glucocorticosteroid compound as an effective agent and a dispersion stabilizer and/or a viscosity modifier as an additive.

The "aqueous pharmaceutical composition" herein means an aqueous liquid or gel pharmaceutical composition, specifically a pharmaceutical composition containing nanoparticles of a glucocorticosteroid compound suspended in the aqueous liquid or gel. The pharmaceutical composition herein accordingly means an aqueous pharmaceutical composition unless otherwise stated. The aqueous pharmaceutical composition includes injections and topical preparations. The topical preparations herein accordingly mean aqueous preparations for topical administrations. The aqueous pharmaceutical composition may be viscous as long as not preventing the composition from using as a pharmaceutical drug, and includes gel preparations as well as watery preparations.

The "topical area" herein means a part of the body, including an affected site, an area around the affected site or an organ including the affected site, and preferably is the eye, ear, nose (upper respiratory tract) or lung (lower respiratory tract).

The injection may be for treating or preventing a systemic or topical inflammatory or infectious disease, and includes injections such as intravenous injections, subcutaneous injections, intramuscular injections, and intravenous drips.

The "topical preparation" herein means a pharmaceutical composition aimed to be administered locally. The topical preparation preferably includes topical eye preparations (e.g., eye drops), topical ear preparations (e.g., ear drops), topical nose preparations (e.g., nose drops) and topical lung preparations (e.g., inhalers). These topical preparations can be used to treat or prevent inflammatory or infectious diseases of the eye, ear, nose or lung. The preparation form also includes eye drops, ear drops, nose drops and inhalers. The topical preparations may preferably be topical eye preparations (including eye drops) for treating or preventing ocular inflammatory or infectious diseases, topical ear preparations (including ear drops) for treating or preventing otogenic inflammatory or infectious diseases, topical nose preparations (including nose drops) for treating or preventing nasal inflammatory or infectious diseases or topical lung preparations (including inhalers) for treating or preventing pulmonary inflammatory or infectious diseases.

The aqueous pharmaceutical composition can be used to treat or prevent inflammatory or infectious diseases by topically administering an effective amount thereof to a patient in need thereof. In other words, the present invention relates to, in one embodiment, a method for treatment or prevention of inflammatory or infectious diseases comprising administering an effective amount of the aqueous suspension or the pharmaceutical composition containing the aqueous suspension, wherein the aqueous suspension or pharmaceutical composition contains nanoparticles of a glucocorticosteroid compound and optionally a dispersion stabilizer and/or a viscosity modifier to a patient in need thereof. The present invention, for example, encompasses a method for treatment or prevention of inflammatory or infectious diseases comprising topically administering an effective amount of the topical preparation containing nanoparticles of a glucocorticosteroid compound and optionally a dispersion stabilizer to a patient in need thereof.

Alternatively, the present invention relates to a use of nanoparticles of a glucocorticosteroid compound (optionally with a dispersion stabilizer and/or a viscosity modifier) or a use of an aqueous suspension containing said nanoparticles, for manufacturing an aqueous pharmaceutical composition (e.g., injections and topical preparations).

The "glucocorticosteroid compound" herein is not limited as long as it is glucocorticosteroid and derivatives thereof. Examples of the glucocorticosteroid compound include clobetasol propionate, diflorasone diacetate, dexamethasone propionate, difluprednate, mometasone furoate, diflucortolone valerate, betamethasone butyrate propionate, fluocinonide, hydrocortisone butyrate propionate, beclomethasone dipropionate, deprodone propionate, betamethasone valerate, dexamethasone valerate, prednisolone valerate acetate, fluocinolone acetonide, hydrocortisone butyrate, clobetasone butyrate, alclometasone dipropionate, triamcinolone acetonide, flumethasone pivalate, prednisolone and hydrocortisone, and clobetasol propionate is preferable.

The "aqueous suspension" herein means an aqueous liquid in which nanoparticles of a glucocorticosteroid compound are suspended. The aqueous suspension herein may constitute a pharmaceutical composition which can be administered as a pharmaceutical drug by itself, or may constitute a pharmaceutical composition by adding other components and a diluent (e.g. raw materials for pharmaceutical composition), or may not be used for a pharmaceutical drug.

The aqueous suspension herein includes dispersion-stabilized aqueous suspensions. The dispersion-stabilized means that the aqueous suspension has any one of, or two or more of, the properties of (1) no precipitation confirmed under visual inspection, (2) high transparency, (3) no agglomerate or crystal observed under microscopic observation, and (4) no substantial changes in the Dv value (not 50% or more increase) after dispersion by stirring followed by standing for 24 hours (preferably 2 days, 3 days, 4 days, 5 days, 6 days, 7 days, 1 month, 2 months, 3 months, 4 months, 5 months, 6 months, 1 year or 2 years) at room temperature (25° C.) The aqueous suspension containing nanoparticles of a glucocorticosteroid compound herein is preferably an aqueous suspension with no precipitation confirmed under visual inspection, high transparency, and no agglomerate or crystal observed under microscopic observation after 7 days from sealed in a test tube.

The transparency can be determined in conformity with the transparency test described in The Japanese Pharmacopoeia. Specifically, the transparency can be determined by the following procedures. Water is added to 5 mL of a formazine standard up to 100 mL, which is used as a turbidity standard. Each of a tested aqueous suspension and a newly prepared turbidity standard is taken to a colorless clear glass flat-bottom test tube having an inner diameter of 15 mm such that the liquid layer has a depth of 30 mm or 40 mm, which is then compared each other by observing from above on a black backdrop in the scattering light. When the transparency of the tested aqueous suspension is the same as water or the solvent used, or when the turbidity of the tested aqueous suspension is lower than the turbidity standard, the transparency is determined to be high. Alternatively, transmittances at 660 nm of a tested aqueous suspension and of a newly prepared turbidity standard are measured by the ultraviolet visible spectrophotometry method using a 50 mm layer cell, with using water or the solvent as the control. When the transmittance of the tested aqueous suspension is higher than the turbidity standard, the transparency of the tested aqueous suspension is determined to be high.

In another embodiment, the topical preparation is a topical eye preparation having transferability into the aqueous humor. The "transferability into the aqueous humor" herein means that a concentration of a glucocorticosteroid compound (average value) in the aqueous humor is 45 ng/mL or more (preferably 50 ng/mL or more, 55 ng/mL or more, 60 ng/mL or more, 65 ng/mL or more, 70 ng/mL or more, 75 ng/mL or more) after 60 minutes from a single eye drop administration of the aqueous topical preparation containing a glucocorticosteroid compound adjusted to be 0.05% (w/v). The "transferability into the aqueous humor" alternatively may mean that a concentration of glucocorticosteroid compound (average value) in the aqueous humor is 40 ng/mL or more (preferably 50 ng/mL or more, 55 ng/mL or more, 60 ng/mL or more, 63 ng/mL or more, 64 ng/mL or more, 65 ng/mL or more, 70 ng/mL or more, 75 ng/mL or more) after 30 minutes from a single eye drop administration of the aqueous topical preparation containing a glucocorticosteroid compound adjusted to be 0.05% (w/v).

In another embodiment, the topical preparation is a topical eye preparation having transferability into the conjunctiva. The "transferability into the conjunctiva" herein means that a concentration of a glucocorticosteroid compound (average value) in the conjunctiva is 500 ng/mL or more (preferably 659 ng/mL or more, 900 ng/mL or more, 972 ng/mL or more, 1000 ng/mL or more, 1200 ng/mL or more, 1210 ng/mL or more, 1400 ng/mL or more, 1455 ng/mL or more, 1500 ng/mL or more or 2000 ng/mL or more, 2141 ng/mL or more) after 15 minutes from a single eye drop administration of the aqueous topical preparation containing a glucocorticosteroid compound adjusted to be 0.05% (w/v).

The transferability into the aqueous humor and the conjunctiva can be determined according to the method described in the Examples of this application by using appropriate animals, and for example by the following procedures. The lower eyelid of a rabbit is gently pulled off, an eye drop of the test substance is administered (a single eye drop administration) into the conjunctival sac of the left eye using a pipette, and after administration, the upper and lower eyelids are gently closed and held for about 2 seconds. After 15 minutes, 30 minutes, 60 minutes and 90 minutes from the administration, the rabbits are anesthetized and euthanized by bleeding, followed by thoroughly washing the eye with water for injection, and the aqueous humor and conjunctiva are collected. A concentration of glucocorticosteroid compound in the collected aqueous humor can be determined by adding methanol and an internal standard (prednisolone) solution to the collected aqueous humor, stirring the mixture, subsequently adding acetonitrile thereto, stirring the mixture, and centrifuging (13,100×g, 4° C., 5 minutes) the mixture, followed by measuring the supernatant obtained by centrifuge by the LC-MS/MS method. A concentration of the glucocorticosteroid compound in the collected conjunctiva can be determined by adding ultrapure water in nine fold volume of the wet weight of the obtained conjunctiva, homogenizing, further adding methanol and an internal standard (prednisolone) solution thereto, stirring the mixture, subsequently adding acetonitrile thereto, stirring the mixture, and centrifuging the mixture (13100×g, 4° C., 5 minutes), followed by measuring the supernatant obtained by centrifuge by the LC-MS/MS method.

In another embodiment, the topical preparation is a topical eye preparation capable of reducing an increase rate of protein concentration in the aqueous humor. Being "capable of reducing an increase rate of protein concentration in the aqueous humor" means that a protein concentration in the aqueous humor which is obtained by administering 40 μL of the aqueous topical preparation containing a 0.05% (w/v) or 0.1% (w/v) glucocorticosteroid compound seven times at 30-60 minutes intervals before and after keratocentesis (preferably, setting the time of keratocentesis as 0 minutes, seven administrations at 180 minutes, 120 minutes, 60 minutes and 30 minutes before the keratocentesis, and 30 minutes, 60 minutes and 90 minutes after the keratocentesis) to an experimental animal (e.g., rabbit) and collecting the aqueous humor after 30 minutes from the final administration, is less than three times (preferably less than 2.5 times or less than two times) of the protein concentration in the aqueous humor of the eye to which keratocentesis is not carried out.

In another embodiment, the topical preparation is a topical eye preparation capable of inhibiting an inflammation of the eye. Specifically, the topical preparation is a topical eye preparation capable of suppressing a production of prostaglandin E2 (PGE2) that is an inflammation mediator. Being "capable of suppressing a production of PGE2" means that a PGE2 concentration in the aqueous humor which is obtained by administering 40 μL of the aqueous topical preparation containing a 0.05% (w/v) or 0.1% (w/v) glucocorticosteroid compound seven times at 30-60 minute intervals before and after keratocentesis (preferably, setting the time of keratocentesis as 0 minutes, seven administrations at 180 minutes, 120 minutes, 60 minutes and 30 minutes before the keratocentesis, and 30 minutes, 60 minutes and 90 minutes after the keratocentesis) to an experimental animal (e.g., rabbit) and collecting the aqueous humor after 30 minutes from the final administration, is lower than the PGE2 concentration in the aqueous humor obtained by the same manner with administering Durezol (Registered trademark).

The topical eye preparation may have two or more (two, three or all) properties selected from the transferability into the aqueous humor, the transferability into the conjunctiva, the reduction of increase rate of a protein concentration in the aqueous humor and the inflammation inhibitory activity on the eye.

In one embodiment, the aqueous suspension is an aqueous suspension with low irritability. The low irritability herein means that a degree of irritating reactions (inflammation reactions such as flare, swelling and/or congestion) in administering the aqueous suspension to a subject is lower than that in administering previously used aqueous preparations containing the same active component. Whether the irritability of a test aqueous suspension is low or not can be determined, for example, with referring to the method of Jonas, J. Kuehne et al., Am J Ophthalmol (2004) 138:547-553, by administering the test aqueous suspension to the eye of a rabbit, measuring the degree of eye inflammation, and determining that the irritability is low, when the degree of inflammation is lower than the standard liquid agent (the same as above). More specifically, in case of an eye drop, the irritability is determined by applying a preparation containing 1.0% glucocorticosteroid compound to the eye once to 20 times a day at intervals of 30 minutes to several hours, observing the cornea, iris and conjunctiva before administration and 1, 3, 5 and 24 hours after the final administration, and scoring in accordance with Draize's scoring criteria (see OECD GUIDELINES FOR TESTING OF CHEMICALS 405 (24 Feb. 1987) Acute Eye Irritation/Corrosion).

The aqueous suspension or pharmaceutical composition may contain one or two or more physiologically acceptable salts. Examples of the "physiologically acceptable salt" include sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate, and dipotassium hydrogen phosphate, and sodium chloride is preferable.

The aqueous suspension or pharmaceutical composition can contain the physiologically acceptable salt at a concentration of 0.01 to 10%, preferably 0.1 to 5% or, for example, 0.5 to 3%, 0.8 to 2%. Alternatively, the aqueous suspension or pharmaceutical composition can contain the physiologically acceptable salt at a concentration of 0.01 to 50 mg/mL, 0.1 to 20 mg/mL or 1 to 5 mg/mL.

The aqueous suspension or pharmaceutical composition may contain one or two or more surfactants and/or one or two or more agglomeration inhibitors.

The "surfactant" is not limited as long as it can be administered to a human as a pharmaceutical additive without showing toxicity and without hindering the activity of glucocorticosteroid compound. The surfactant may be, for example, non-ionic surfactant including polyoxyethylene (hereinafter referred to as "POE")-polyoxypropylene (hereinafter referred to as "POP") block copolymers such as poloxamer 407, poloxamer 235 and poloxamer 188; ethylenediamine adducts to polyoxyethylene-polyoxypropylene block copolymer such as poloxamine; POE sorbitan fatty acid esters such as POE (20) sorbitan monolaurate (polysorbate 20), POE (20) sorbitan monooleate (polysorbate 80) and polysorbate 60; POE hydrogenated castor oils such as POE (60) hydrogenated castor oil; POE alkyl ethers such as POE (9) lauryl ether; POE-POP alkyl ethers such as POE (20) POP (4) cetyl ether; POE alkylphenyl ethers such as POE (10) nonyl phenyl ether; POE-POP glycols such as POE (105) POP (5) glycol, POE (120) POP (40) glycol, POE (160) POP (30) glycol, POE (20) POP (20) glycol, POE (200) POP (70) glycol, POE (3) POP (17) glycol, POE (42) POP (67) glycol, POE (54) POP (39) glycol and POE (196) POP (67) glycol; amphoteric surfactants including glycine-type surfactants such as alkyldiaminoethyl glycine, betaine acetate-type surfactants such as lauryl dimethylaminoacetic acid betaine, and imidazoline-type surfactants; anionic surfactants including POE alkyl ether phosphates and salts thereof such as POE (10) sodium lauryl ether phosphate, N-acylamino acid salts such as sodium lauroyl methyl alanine, alkyl ether carboxylates, N-acyl taurates such as sodium cocoyl N-methyltaurate, sulfonates such as sodium tetradecenesulfonate, alkyl sulfates such as sodium lauryl sulfate, POE alkyl ether sulfates such as POE (3) sodium lauryl ether sulfate, and α-olefin sulfonates; and cationic surfactants including alkylamine salts, alkyl quarternary ammonium salts (benzalkonium chloride and benzethonium chloride) and alkyl pyridinium salts (cetylpyridinium chloride and cetylpyridinium bromide). The aqueous suspension may contain one or two or more surfactants.

The "agglomeration inhibitor" herein is not limited as long as it inhibits an agglomeration of the glucocorticosteroid compound and it can be administered to a human without showing toxicity and without hindering the activity of glucocorticosteroid compound. The agglomeration inhibitor may be phospholipids such as alkyl sulfate, N-alkyloyl methyl taurate, ethanol, glycerol, propylene glycol, sodium citrate, phospholipids including glycerophospholipid (lecithin (phosphatidylcholine) (e.g., refined soybean lecithin, hydrogenated soybean lecithin), phosphatidylserine, phosphatidylethanolamine, phosphatidylinositol, phosphatidic acid, phosphatidylglycerol, lysophosphatidylcholine, lysophosphatidylserine, lysophosphatidylethanolamine, lysophosphatidylinositol, lysophosphatidic acid and lysophosphatidylglycerol) and sphingophospholipids (sphingomyelin, ceramide, glycosphingolipid or ganglioside), D-sorbitol, lactose, xylitol, gum arabic, sucrose fatty acid ester, polyoxyethylene hydrogenated castor oil, polyoxyethylene fatty acid esters, polyethyleneglycol (PEG), polyoxyethylene sorbitan fatty acid ester, alkyl benzene sulfonate, sulfosuccinate, POE-POP glycol, polyvinylpyrrolidone, PVA, hydroxypropyl cellulose, methyl cellulose, hydroxyethyl cellulose, hydroxypropyl methylcellulose, carmellose sodium, carboxyvinyl polymers, N-acyl-glutamate, acrylic acid copolymers, methacrylic acid copolymers, casein sodium, L-valine, L-leucine, L-isoleucine, benzalkonium chloride and benzethonium chloride. The aqueous suspension may contain one agglomeration inhibitor or two or more agglomeration inhibitors.

The aqueous suspension or pharmaceutical composition can contain agglomeration inhibitor at a concentration of 0.001 to 10% or 0.01 to 10%, preferably 0.02 to 5%, for example, 0.03 to 1%, 0.04 to 0.5%, 0.05 to 0.2%. Alternatively, the aqueous suspension or pharmaceutical composition can contain the agglomeration inhibitor at a concentration of 0.01 to 50 mg/mL, 0.1 to 20 mg/mL or 1 to 5 mg/mL.

The surfactant and/or the agglomeration inhibitor are preferably one or more substances selected from polyoxyethylene hydrogenated castor oil 60 (e.g., HCO-60), polyoxyethylene hydrogenated castor oil 40 (e.g., HCO-40), polysorbate 80 (e.g., Tween 80), polysorbate 20 (e.g., Tween 20), POE-POP glycol (e.g., PLONON 407P, Pluronic F68, UNILUB 70DP-950B) and PVA (e.g., Kuraray POVAL 217C), and more preferably one or more substances selected from POE-POP glycol and PVA.

The "viscosity modifier" herein is not limited as long as it is capable of adjusting the viscosity of the aqueous suspension and it can be administered to a human as a pharmaceutical additive without showing toxicity and without hindering the activity of the glucocorticosteroid compound. The viscosity modifier may be polysaccharides or derivatives thereof (gum arabic, gum karaya, xanthan gum, carob gum, guar gum, gum guaiac, quince seed, darman gum, gum tragacanth, benzoin rubber, locust bean gum, casein, agar, alginic acid, dextrin, dextran, carrageenan, gelatin, collagen, pectin, starch, polygalacturonic acid, chitin and derivatives thereof, chitosan and derivatives thereof, elastin, heparin, heparinoid, heparin sulfate, heparan sulfate, hyaluronic acid and chondroitin sulfate), ceramide, cellulose derivatives (methyl cellulose, ethyl cellulose, hydroxyethyl cellulose, hydroxypropyl cellulose, hydroxypropyl methylcellulose, carboxymethyl cellulose, carboxyethyl cellulose, cellulose and nitrocellulose), PVA (completely or partially saponified), polyvinylpyrrolidone, Macrogol, polyvinyl methacrylate, polyacrylic acid, carboxyvinyl polymer, polyethyleneimine, polyethylene oxide, polyethylene glycol, ribonucleic acid, deoxyribonucleic acid, methyl vinyl ether-maleic anhydride copolymers, and pharmacologically acceptable salts thereof (e.g., sodium alginate). The aqueous suspension may contain one or two or more viscosity modifiers. The viscosity modifier is preferably one or more substances selected from hydroxypropyl methylcellulose (e.g., TC-5(R), Metlose 60SH-50), PVA (Kuraray POVAL 217C) and methyl cellulose (e.g., Metlose SM-100, Metlose SM-15), with one or more substances selected from hydroxypropyl methylcellulose and methyl cellulose being more preferable.

The aqueous suspension can contain 1 to 10 mg/mL, preferably 1 to 5 mg/mL, for example, 1 to 4 mg/mL, 1 to 3 mg/mL, 1 to 2 mg/mL, of the viscosity modifier.

The dispersion stabilizer usable herein is the substances listed above as the surfactants, agglomeration inhibitors and/or viscosity modifiers, and is preferably one or more substances selected from polyoxyethylene hydrogenated castor oil 60, polyoxyethylene hydrogenated castor oil 40, polysorbate 80, polysorbate 20, POE-POP glycol, PVA, hydroxypropyl methylcellulose and methyl cellulose, and more preferably one or more substances selected from POE-POP glycol, PVA, hydroxypropyl methylcellulose and methyl cellulose.

The surfactant, agglomeration inhibitor and/or viscosity modifier which are also used as the dispersion stabilizer (hereinafter referred to as "additives" in this paragraph) may adhere to or be adsorbed on the surface of nanoparticles of a glucocorticosteroid compound. When these additives are added before the pulverization step, these additives adhere to or are adsorbed on the surface of nanoparticles of a glucocorticosteroid compound, which results in inhibiting the nanoparticle agglomeration during the pulverization step. By adhering to or by adsorbing on the surface of nanoparticles of a glucocorticosteroid compound, the additives effectively inhibit the agglomeration in the aqueous suspension. In this context, the surfactant, agglomeration inhibitor and/or viscosity modifier which can be also used as the dispersion stabilizer can be construed to adhere to or to be adsorbed on the surface of nanoparticles of a glucocorticosteroid compound, as long as at least a part of the additives adheres to or is adsorbed on the nanoparticle surface (contributing to the surface modification), and it is not necessary that the additive neither adhering nor being adsorbed is not present in the aqueous suspension. The "surface modifier" herein refers to the surfactant, the agglomeration inhibitor and/or the viscosity modifier which can be the dispersion stabilizer, which is capable of modifying the nanoparticle surface of a glucocorticosteroid compound.

The aqueous suspension or pharmaceutical composition may contain one or two or more physiologically acceptable polyols. The pharmaceutical composition may contain, for example, the physiologically acceptable polyols described above. The "physiologically acceptable polyols" include glycerin, propylene glycol, polyethylene glycol, dipropylene glycol and diethylene glycol, and preferably is propylene glycol or glycerin. The aqueous suspension or pharmaceutical composition can contain the physiologically acceptable polyol at a concentration of, for example, 0.001 to 10% or 0.01 to 10%, preferably, 0.02 to 5%, for example, 0.03 to 1%, 0.04 to 0.5%, 0.05 to 0.2%. Alternatively, the aqueous suspension or pharmaceutical composition can contain the physiologically acceptable polyol at a concentration of 0.01 to 10 mg/mL, 0.05 to 5 mg/mL or 0.1 to 3 mg/mL.

The aqueous suspension or aqueous pharmaceutical composition does not contain an oil solvent. The oil solvent means a water-insoluble or slightly water-soluble solvent.

The glucocorticosteroid compound contained in the aqueous suspension or aqueous pharmaceutical composition is in the form of nanoparticles. The mean particle diameter (Dv) of the glucocorticosteroid compound nanoparticles may be 300 nm or less, preferably 250 nm or less, 240 nm or less, 230 nm or less, 220 nm or less, 210 nm or less, 200 nm or less, 190 nm or less, 180 nm or less, 170 nm or less, 160 nm or less, 150 nm or less, 140 nm or less, 130 nm or less, 120 nm or less or 110 nm or less. The ranges of mean particle diameter of the glucocorticosteroid compound may be, for example, 50 to 300 nm, 50 to 250 nm, 50 to 240 nm, 50 to 230 nm, 50 to 220 nm, 50 to 210 nm, 50 to 200 nm, 50 to 190 nm, 50 to 180 nm, 50 to 170 nm, 50 to 160 nm, 50 to 150 nm, 50 to 140 nm, 50 to 130 nm, 50 to 120 nm, 50 to 110 nm, 100 to 300 nm, 100 to 250 nm, 100 to 240 nm, 100 to 230 nm, 100 to 220 nm, 100 to 210 nm, 100 to 200 nm, 100 to 190 nm, 100 to 180 nm, 100 to 170 nm, 100 to 160 nm, 100 to 150 nm, 100 to 140 nm, 100 to 130 nm, 100 to 120 nm or 100 to 110 nm.

The 90% diameter (D90) of the glucocorticosteroid compound nanoparticles contained in the aqueous suspension or aqueous pharmaceutical composition is 450 nm or less, preferably 400 nm or less, 350 nm or less, 300 nm or less, 290 nm or less, 280 nm or less, 270 nm or less, 260 nm or less, 250 nm or less, 240 nm or less or 230 nm or less. The ranges of 90% diameter (D90) of the glucocorticosteroid compound may be, for example, 50 to 400 nm, 50 to 350 nm, 50 to 300 nm, 50 to 290 nm, 50 to 280 nm, 50 to 270 nm, 50 to 260 nm, 50 to 250 nm, 50 to 240 nm, 50 to 230 nm, 100 to 400 nm, 100 to 350 nm, 100 to 300 nm, 100 to 290 nm, 100 to 280 nm, 100 to 270 nm, 100 to 260 nm, 100 to 250 nm, 100 to 240 nm or 100 to 230 nm.

The 50% diameter (D50) of the glucocorticosteroid compound nanoparticles contained in the aqueous suspension or aqueous pharmaceutical composition may be 200 nm or less, preferably 190 nm or less, 180 nm or less, 170 nm or less, 160 nm or less, 150 nm or less, 140 nm or less, 130 nm or less, 120 nm or less, 110 nm or less or 100 nm or less. The ranges of 50% diameter (D50) of the glucocorticosteroid compound may be 50 to 190 nm, 50 to 180 nm, 50 to 170 nm, 50 to 160 nm, 50 to 150 nm, 50 to 140 nm, 50 to 130 nm, 50 to 120 nm, 50 to 110 nm, 50 to 100 nm, 80 to 190 nm, 80 to 180 nm, 80 to 170 nm, 80 to 160 nm, 80 to 150 nm, 80 to 140 nm, 80 to 130 nm, 80 to 120 nm, 80 to 110 nm or 80 to 100 nm.

The glucocorticosteroid compound nanoparticles contained in the aqueous suspension or aqueous pharmaceutical composition may meet two or more particle diameter conditions selected from the mean particle diameter (Dv), the 90% diameter (D90) and the 50% diameter (D50) described above. The glucocorticosteroid compound nanoparticles contained in the aqueous suspension can have, for example, a mean particle dimeter (Dv) of 166 nm or less, a D50 of 138 nm or less and/or a D90 of 241 nm or less. The glucocorticosteroid compound nanoparticles contained in the aqueous pharmaceutical composition can have, for example, a mean particle dimeter (Dv) of 204 nm or less, a D50 of 177 nm or less and/or a D90 of 306 nm or less.

The glucocorticosteroid compound contained in the aqueous suspension as the active component is in the form of nanoparticles, which enables the aqueous suspension to be filter-sterilized, and thus the aqueous suspension can be sterilized easily and hardly affecting the physicochemical properties of the active component.

The nanoparticle of a glucocorticosteroid compound contained in the aqueous suspension is preferably those produced by mixing a glucocorticosteroid compound, a physiologically acceptable salt, a physiologically acceptable polyol and a dispersion stabilizer. More preferably, the nanoparticle of a glucocorticosteroid compound is those produced by mixing a glucocorticosteroid compound, a physiologically acceptable salt, a physiologically acceptable polyol and a dispersion stabilizer, with adding lecithin (e.g., hydrogenated soybean lecithin) during or after pulverization.

The aqueous suspension includes, for example, a preparation containing, nanoparticles of a glucocorticosteroid compound; sodium chloride; hydrogenated soybean lecithin; glycerin; anhydrous citric acid; one or more substances selected from POE-POP glycols, polyoxyethylene hydrogenated castor oils, Polysorbate 80, PVA and POE-POP block copolymers; benzalkonium chloride, sorbic acid or salts thereof (potassium sorbate, sodium sorbate and triclocarban sorbate) or paraoxybenzoates (methyl parahydroxybenzoate, ethyl parahydroxybenzoate, propyl parahydroxybenzoate and butyl parahydroxybenzoate); hydroxypropyl methylcellulose and/or methyl cellulose; and sodium citrate (including trisodium citrate).

The aqueous suspension and the pharmaceutical composition can contain water as the main component. The pharmaceutical composition, the aqueous suspension and/or the diluent herein may contain, as necessary, various additives such as a stabilizer, a flavoring agent, a thickener, a surfactant, a preservative, a disinfectant or antibacterial agent, a pH control agent, a tonicity agent and a buffer.

The preservative and the disinfectant or antibacterial agent include sorbic acids or salts thereof (potassium sorbate, sodium sorbate and triclocarban sorbate), paraoxybenzoates (methyl parahydroxybenzoate, ethyl parahydroxybenzoate, propyl parahydroxybenzoate and butyl parahydroxybenzoate), acrinol, methylrosanilinium chloride, benzalkonium chloride, benzethonium chloride, cetylpyridinium chloride, cetylpyridinium bromide, chlorhexidine or salts thereof, polyhexamethylene biguanide, alkylpolyaminoethylglycine, benzyl alcohol, phenethyl alcohol, chlorobutanol, isopropanol, ethanol, phenoxyethanol, silver supported on zirconium phosphate, mercurochrome, povidone iodine, thimerosal, dehydroacetic acid, chloroxylenol, chlorophen, resorcinol, orthophenylphenol, isopropylmethylphenol, thymol, hinokitiol, sulfamine, lysozyme, lactoferrin, triclosan, 8-hydroxyquinoline, undecylenic acid, caprylic acid, propionic acid, benzoic acid, halocarban, thiabendazole, polymyxin B, 5-chloro-2-methyl-4-isothiazolin-3-one, 2-methyl-4-isothiazolin-3-one, polylysine, hydrogen peroxide, polidronium chloride, Glokill (tradename: e.g., Glokill PQ, Rhodia), polydiaryl dimethyl ammonium chloride, poly[oxyethylene(dimethyliminio)ethylene-(dimethyliminio)ethylene dichloride], polyethylene polyamine-dimethylamine epichlorohydrin polycondensates (tradename: e.g., Busan 1157, Buckman Laboratories International, Inc.) and biguanide compounds (Cosmocil CQ (tradename, about 20 wt % content of polyhexamethylenebiguanide hydrochloride, Arch Personal Care Products L.P.)), and pharmacologically acceptable salts thereof. Benzalkonium chloride is preferable.

The pH control agent include inorganic acids (hydrochloric acid, sulfuric acid, phosphoric acid, polyphosphoric acid and boric acid), organic acids (lactic acid, acetic acid, citric acid, anhydrous citric acid, tartaric acid, malic acid, succinic acid, oxalic acid, gluconic acid, fumaric acid, propionic acid, aspartic acid, epsilon-aminocaproic acid, glutamic acid and aminoethylsulfonic acid), gluconolactone, ammonium acetate, inorganic bases, (sodium hydrogen carbonate, sodium carbonate, potassium hydroxide, sodium hydroxide, calcium hydroxide and magnesium hydroxide), organic bases (monoethanolamine, triethanolamine, diisopropanolamine, triisopropanolamine and lysine), borax, and pharmacologically acceptable salts thereof.

The tonicity agent includes inorganic salts (sodium chloride, potassium chloride, sodium carbonate, sodium hydrogen carbonate, calcium chloride, magnesium sulfate, sodium hydrogen phosphate, disodium hydrogen phosphate, dipotassium hydrogen phosphate, sodium thiosulfate and sodium acetate), polyhydric alcohols (glycerin, propylene glycol, ethylene glycol and 1,3-butylene glycol), saccharides (glucose, mannitol and sorbitol).

The buffer includes tris buffer, borate buffer, phosphate buffer, carbonate buffer, citrate buffer, acetate buffer, epsilon-aminocaproic acid and aspartate. Specific examples include boric acid or salts thereof (sodium borate, potassium tetraborate and potassium metaborate), phosphoric acid or salts thereof (sodium hydrogen phosphate, sodium dihydrogen phosphate and potassium dihydrogen phosphate), carbonic acid or salts thereof (sodium hydrogen carbonate and sodium carbonate), citric acid or salts thereof (sodium citrate, potassium citrate and anhydrous citric acid).

The viscosity of the aqueous suspension and the pharmaceutical composition herein can be 1 to 5 mPa·s, and may be, for example, 1 to 3 mPa·s.

The "%" as used herein in the composition or the content refers to weight % (w/w), unless otherwise stated.

Advantageous Effects of Invention

The aqueous suspension containing nanoparticles of the glucocorticosteroid compound of the present invention has advantages in transparency, dispersibility, storage stability, transferability into the conjunctiva, and transferability into the aqueous humor, with low irritability, and thus is easily sterilized and has good temporal stability and dispersion stability. The suspension can be used for pharmaceutical compositions for parenteral administration, specifically for eye drops.

BRIEF DESCRIPTION OF DRAWINGS

FIG. 1 is a graph showing the time course change of clobetasol propionate concentration in aqueous humor after ophthalmic administration of the nanosuspension eye drop prepared in Examples 5(1) to 5(3). The ordinate represents the clobetasol propionate concentration (ng/mL) in aqueous humor, and the abscissa represents the elapsed time (minutes) after the administration. The black circles indicate a 0.05% ophthalmic nanosuspension (mean particle diameter 100 nm), the black squares indicate a 0.05% ophthalmic nanosuspension (mean particle diameter 300 nm), and the black triangles indicate a 0.05% ophthalmic nanosuspension (mean particle diameter 600 nm). The indicated values are average, and the error bars indicate standard deviations.

FIG. 2 is a graph showing the time course change of clobetasol propionate concentration in conjunctiva after ophthalmic administration of the nanosuspension eye drop prepared in Examples 5(1) to 5(3). The ordinate represents the clobetasol propionate concentration (ng/mL) in conjunctiva, and the abscissa represents the elapsed time (minutes) after the administration. The black circles indicate a 0.05% ophthalmic nanosuspension (mean particle diameter 100 nm), the black squares indicate a 0.05% ophthalmic nanosuspension (mean particle diameter 300 nm), and the black triangles indicate a 0.05% ophthalmic nanosuspension (mean particle diameter 600 nm). The indicated values are average, and the error bars indicate standard deviations.

FIG. 3 is a graph showing the time course change of clobetasol propionate concentration in aqueous humor after ophthalmic administration of nanosuspension eye drop prepared in Examples 7(1) to 7(4). The ordinate represents the clobetasol propionate concentration (ng/mL) in aqueous humor, and the abscissa represents the elapsed time (minutes) after the administration. The white circles indicate a 0.05% ophthalmic nanosuspension P (HPMC (60SH-50) 3 mg/mL), the black circles indicate a 0.05% ophthalmic nanosuspension Q (HPMC (60SH-4000) 1.5 mg/mL), the white triangles indicate a 0.05% ophthalmic nanosuspension R (MC (SM-100) 2 mg/mL), and the black triangles indicate a 0.05% ophthalmic nanosuspension S (MC (SM-4000) 1.5 mg/mL). The indicated values are average, and the error bars indicate standard deviations.

FIG. 4 is a graph showing the time course change in clobetasol propionate concentration in conjunctiva after ophthalmic administration of nanosuspension eye drop prepared in Examples 7(1) to 7(4). The ordinate represents the clobetasol propionate concentration (ng/mL) in conjunctiva, and the abscissa represents the elapsed time (minutes) after the administration. The white circles indicate a 0.05% ophthalmic nanosuspension P (HPMC (60SH-50) 3 mg/mL), the black circles indicate a 0.05% ophthalmic nanosuspension Q (HPMC (60SH-4000) 1.5 mg/mL), the white triangles indicate a 0.05% ophthalmic nanosuspension R (MC (SM-100) 2 mg/mL), and the black triangles indicate a 0.05% ophthalmic nanosuspension S (MC (SM-4000) 1.5 mg/mL). The indicated values are average, and the error bars indicate standard deviations.

FIG. 5 is a graph showing the inflammation score of the external eye for a rabbit model of BSA-induced uveitis. The ordinate represents the inflammation score, and the abscissa represents the elapsed days (from the 15th to 18th day) after the first BSA administration. The white bars indicate a control group (physiological saline solution), the dark gray bars indicate a 0.05% clobetasol propionate ophthalmic nanosuspension administration group, and the pale gray bars indicate a positive control group (0.1% fluorometholone ophthalmic solution administration group). The indicated values are average, and the error bars indicate standard deviations.

FIG. 6 is a graph showing the inflammation score of the internal eye for a rabbit model of BSA-induced uveitis. The ordinate represents the inflammation score, and the abscissa represents the elapsed days (from the 15th to 18th day) after the first BSA administration. The white bars indicate a control group (physiological saline solution), the dark gray bars indicate a 0.05% clobetasol propionate ophthalmic nanosuspension administration group, and the pale gray bars indicate a positive control group (0.1% fluorometholone ophthalmic solution administration group). The indicated values are average, and the error bars indicate standard deviations.

FIG. 7 presents graphs showing the inflammation scores of the external eye (A) and internal eye (B) on the 29th day after the first BSA administration for a rabbit model of BSA-induced uveitis. The ordinates represent the inflammation scores. The white bars indicate a control group (physiological saline solution), the dark gray bars indicate a 0.05% clobetasol propionate ophthalmic nanosuspension administration group, and the pale gray bars indicate a positive control group (0.1% fluorometholone ophthalmic solution administration group). The indicated values are average, and the error bars indicate standard deviations.

FIG. 8 is a graph showing the conjunctival weight for a rat model of croton-induced conjunctivitis. The ordinate represents the conjunctival weight (g). The indicated values are average, and the error bars indicate standard deviations.

FIG. 9 is a graph showing the palpebral conjunctival weight for a rat model of carrageenan-induced conjunctival edema. The ordinate represents the palpebral conjunctival weight (g). The indicated values are average, and the error bars indicate standard deviations.

FIG. 10 is a graph showing the PGE2 concentration in aqueous humor for a rabbit model of LPS-induced uveitis. The ordinate represents the PGE2 concentration (pg/mL) in aqueous humor. The indicated values are average, and the error bars indicate standard deviations.

FIG. 11 is a graph showing the PGE2 concentration in vitreous body for a rabbit model of LPS-induced uveitis. The ordinate represents the PGE2 concentration (pg/mL) in vitreous body. The indicated values are average, and the error bars indicate standard deviations.

FIG. 12 is a graph showing the protein concentration in aqueous humor for a rabbit model of puncture-induced anterior chamber inflammation. The ordinate represents the protein concentration (mg/mL) in anterior chamber aqueous humor. The indicated values are average, and the error bars indicate standard deviations.

FIG. 13 is a graph showing the PGE2 concentration in vitreous body for a rabbit model of LPS-induced uveitis. The ordinate represents the PGE2 concentration (pg/mL) in vitreous body. The indicated values are average, "b.i.d" means twice administration per day, and "q.i.d" means four-times administration per day.

DESCRIPTION OF EMBODIMENTS

1. Aqueous Suspension Containing Nanoparticles of a Glucocorticosteroid Compound The nanoparticle of a glucocorticosteroid compound can be produced by mixing the glucocorticosteroid compound with a physiologically acceptable salt and a physiologically acceptable polyol, and wet pulverizing the organic compound. The production method is described in detail in International Publication No. WO 2008/126797. The mixing step only requires that glucocorticosteroid compound, the physiologically acceptable salt and the physiologically acceptable polyol are all mixed together in the end, and an order of addition is not limited. The mixing step may be achieved by, for example, adding the physiologically acceptable salt and the physiologically acceptable polyol to the glucocorticosteroid compound or alternatively by adding the glucocorticosteroid compound to the physiologically acceptable salt and the physiologically acceptable polyol. The glucocorticosteroid compound nanoparticles contained in a powder of the present invention can be produced by adding the physiologically acceptable salt and the physiologically acceptable polyol to an organic compound having a melting point of 80° C. or more, and wet pulverizing the organic compound. In this method, the aqueous suspension can be prepared without removing the salt and the polyol. Since there is no need to remove the salt and the polyol, the suspension can be prepared by very simple steps. The wet pulverization is achieved by mixing the organic compound, the salt and the polyol, and kneading the mixture. The nanoparticle of a glucocorticosteroid compound can be preferably produced by adding lecithin during or after the pulverization step.

The glucocorticosteroid compound nanoparticle is produced preferably by wet pulverization without using a hard solid pulverization aid, more preferably without using a solid pulverization aid such as glass products, metallic products such as stainless steel, ceramic products such as zirconia and alumina, and large molecular products such as rigid polystyrene. Most preferably, the glucocorticosteroid compound nanoparticle is produced by wet pulverization without using a solid pulverization aid other than the physiologically acceptable salt and the viscosity modifier.

The "physiologically acceptable" means it is believed not to cause physiological problems being administered into a body. The physiological acceptance of a certain substance is suitably determined depending on the species to be administered the substance as well as modes of administration. Examples of the physiologically acceptable solvent include substances which are approved as additives or solvents for pharmaceutical drugs or for food products.

The "physiologically acceptable salt" herein is not limited as long as it can be administered without causing physiological problems. The physiologically acceptable salt preferably has low solubility to polyols, high solubility to water and/or low moisture absorption with suitable hardness for pulverization of the organic compound. More preferably, the physiologically acceptable salt used in the method for producing the glucocorticosteroid compound nanoparticle has two or more of these properties. The solubility of physiologically acceptable salt to polyols is preferably 10% (mass/volume) or less. The physiologically acceptable salt is preferably highly soluble to water for easy removal after pulverization. Specific examples include the salts listed above in this specification.

The "physiologically acceptable salt" is preferably pulverized for adjusting the particle diameter before mixing with the glucocorticosteroid compound. Moreover, the physiologically acceptable salt may be dried under reduced pressure at a temperature of 30 to 200° C. to reduce a contained water for preventing particle fusion and growth caused by the contained water. When the particle diameter of the physiologically acceptable salt is adjusted in advance, the particle volume mean diameter may be, for example, 5 to 300 μm, 10 to 200 μm, preferably 0.01 to 300 μm, more preferably 0.1 to 100 μm, further preferably 0.5 to 50 μm, most preferably 1 to 5 μm. The amount of salt to be used is preferably 1 to 100 times, more preferably 5 to 30 times, further preferably 10 to 20 times a mass of the glucocorticosteroid compound. One kind of salt may be used singly, or two or more kinds of salts may be used together.

The "physiologically acceptable polyol" used in the method for producing the glucocorticosteroid compound nanoparticles is not limited as long as it can be administered without causing any physiological problems. The preferable physiologically acceptable polyol has low solubility to salts, high solubility to water, a low freezing point and/or a high ignition point. The physiologically acceptable polyol is preferably highly soluble to water for easy removal after pulverization.

The polyol used in the method for producing the glucocorticosteroid compound nanoparticles preferably has a high viscosity. The viscosity of a polyol at 20° C. may be 40 mPa·s or more, preferably 50 mPa·s or more, more preferably 80 mPa·s or more. The upper limit of the viscosity at 20° C. of the polyol to be used in the method for producing the glucocorticosteroid compound nanoparticles is not limited, and, for example, can be selected from the ranges from 40 mPa·s or more to 5,000 mPa·s or less, preferably 50 mPa·s or more to 3,000 mPa·s or less, more preferably 80 mPa·s or more to 2,000 mPa·s or less. Specific examples include the polyols listed above in this specification.

The amount of physiologically acceptable polyol used in the method for producing the glucocorticosteroid compound nanoparticles is preferably 0.5 to 100 times, more preferably 1 to 10 times a mass of the organic compound to be pulverized. The kind of polyol can be suitably determined according to the solubility of the organic compound to be pulverized. One kind of polyol may be used singly, or two or more kinds of polyols may be used together.

In the method for producing nanoparticles of a glucocorticosteroid compound, the kneaded product containing the glucocorticosteroid compound, the polyol and the salt preferably has a high viscosity. The viscosity of the kneaded product can be increased preferably by using the mixture in which a viscosity modifier is added to the polyol, or by adding a viscosity modifier independently from the polyol, which can effectively improve the pulverization efficiency. The viscosity modifiers described in the above can be added to the polyol. The viscosity at 20° C. of a polyol to which the viscosity modifier is added is preferably 1,000 mPa·s or more, more preferably 2,000 mPa·s or more, further preferably 5,000 mPa·s or more, most preferably 10,000 mPa·s or more. The upper limit of the viscosity at 20° C. of the polyol to which the viscosity modifier is added is not limited, and, for example, can be selected from the ranges from 1,000 mPa·s or more to 5,000,000 mPa·s or less, preferably 1,000 mPa·s or more to 1,000,000 mPa·s or less, more preferably 2,000 mPa·s or more to 500,000 mPa·s or less, further preferably 5,000 mPa·s or more to 300,000 mPa·s or less, most preferably 10,000 mPa·s or more to 100,000 mPa·s or less.

In the method for producing the glucocorticosteroid compound nanoparticles, any grinder can be used for wet pulverization of the glucocorticosteroid compound without limitation, as long as it can mechanically knead and disperse the glucocorticosteroid compound, the salt, the polyol and/or the dispersion stabilizer. Examples of the commonly used grinder include kneaders, two rolls, three rolls, fret mills, hoover mullers, and disk blade kneader dispersers.

The pulverization temperature can be suitably determined according to the glucocorticosteroid compound to be pulverized and a type of grinder. The pulverization temperature is not limited, and preferably −50 to 50° C., more preferably −20 to 30° C., and most preferably −10 to 25° C. The pulverization time can be also suitably determined according to the organic compound to be pulverized and a type of grinder. The pulverization time can be, for example, 1 to 50 hours, 2 to 30 hours, 3 to 20 hours, 4 to 18 hours, 5 to 10 hours.

After completion of the pulverization of glucocorticosteroid compound, the objective particles of pulverized glucocorticosteroid compound can be obtained without removing the salt and the polyol which are used for the pulverization. Because washing step is not necessary, nanoparticle preparation is produced simpler at a lower cost. The suspension can be prepared by homogenizing the mixture of the glucocorticosteroid compound, the salt, the polyol and/or the viscosity modifier in a solvent using a homogenizer. The solvent used for homogenizing the mixture is not limited as long as easily dissolving the polyol, the salt and the viscosity modifier but hardly dissolving the pulverized glucocorticosteroid compound and being physiologically acceptable. The solvent is preferably water but any solvent other than water can be used, which includes a mixture of water and an organic solvent such as acetic acid, methanol or ethanol. The homogenized mixture can be filtered, if necessary. The filtration method is not limited and any known filtration method used for filtering organic compounds contained therein can be employed. Examples of the filtration method include a reduced pressure filtration method, an applied pressure filtration method, and an ultrafiltration membrane method.

The pulverized particles typically have a high surface energy and thus easily agglomerate. Thus, the agglomeration inhibitor described above may be added after removing the salts etc. to prevent the secondary agglomeration. One kind of the agglomeration inhibitor may be used singly, or two or more kinds of agglomeration inhibitors may be used together.

After removing the salt and the polyol, the obtained particles of pulverized glucocorticosteroid compound can be dried to remove the solvent used for removing the salt etc. The drying method is not limited and any method commonly used for drying an organic compound can be employed. Examples of the drying method include a reduced pressure drying method, a freeze-drying method, a spray drying method, and a spray-freezing-drying method. The drying temperature and drying time in these drying methods are not limited but is preferably at a low temperature for maintaining the chemical stability of organic compound particles for medical use and preventing the secondary particle agglomeration. By the same reason, freeze-drying method, the spray drying method, and the spray-freezing-drying method are preferable.

The mean particle diameter ranges of the pulverized glucocorticosteroid compound particles obtained by the above production method can be the same as the mean particle diameter of the glucocorticosteroid compound nanoparticles contained in the aqueous suspension or aqueous pharmaceutical composition described above. Also, the ranges of the 90% diameter (D90) and the 50% diameter (D50) of the pulverized glucocorticosteroid compound particles obtained by the above production method can be the same as the 90% diameter (D90) and the 50% diameter (D50), respectively, of the glucocorticosteroid compound nanoparticles contained in the aqueous suspension or aqueous pharmaceutical composition described above.

The "mean particle diameter" or "Dv" herein means the arithmetic mean diameter of the particle size distribution measured by dynamic light scattering photon correlation spectroscopy. The 50% diameter (also referred to as median diameter, D50) represents the diameter at which powder particles are divided into two groups in the particle size distribution measured by the above measurement method, wherein the amounts of particles are equal between said two groups, the larger diameter group and the smaller diameter group. The "90% diameter" means the diameter (D90) of the particle at 90% position in the particle size distribution measured by the above measurement method, wherein the number of particles is counted from the smaller particle diameter to the larger particle diameter, as setting 0% (less smallest) to 100% (the largest particle). The "10% diameter" means the diameter (D10) of the particle at 10% position in the particle size distribution measured by the above measurement method, wherein the number of particles is counted from the smaller particle diameter to the larger particle diameter, as setting 0% (less smallest) to 100% (the largest particle). The measurement method by dynamic light scattering photon correlation spectroscopy, and the calculation method of particle size distribution are well known in the art.

2. Pharmaceutical Composition

The present invention relates to the pharmaceutical composition containing nanoparticles of a glucocorticosteroid compound. The pharmaceutical composition is preferably a pharmaceutical composition for parenteral administrations such as injections or topical preparations. The type of the pharmaceutical composition herein is not limited. Examples of the formulation include topical eye preparations (e.g., eye drops), topical ear preparations (e.g., ear drops), topical nose preparations (e.g., nose drops), suspensions, ointments, creams, gels, inhalers, injections (e.g., injections for intravenous injection, subcutaneous administration, intramuscular injection and intravenous drips). These preparations can be produced in accordance with a conventional method. The pharmaceutical composition preferably contains a dispersion stabilizer. In case of an injection, the formulation may be prepared using the glucocorticosteroid compound nanoparticles suspended in water, and may be suspended in saline or a glucose solution as necessary, which may further be added a dispersant, a buffer or a preservative. The pharmaceutical composition can be formulated as a parenteral administration form including injection for intravenous administration, intramuscular administration or subcutaneous administration, intravenous drip, transdermal absorber, transmucosal absorber, eye drop, ear drop, nose drop or inhaler.

The pharmaceutical composition may contain a pharmacologically acceptable carrier (an additive for preparations). The kind of additives for preparations used for manufacturing the pharmaceutical composition, the proportion of the additives for preparations relative to the active component, or the method for manufacturing the pharmaceutical composition may be suitably selected by the person skilled in the art depending on the composition form. The additive for preparations can be an inorganic or organic, or a solid or liquid substance, and can be typically added in a range from 1 wt % to 90 wt % of the active component weight. Specific examples of such substance include lactose, glucose, mannitol, dextrin, cyclodextrin, starch, sucrose, magnesium aluminometasilicate, synthetic aluminum silicate, sodium carboxymethyl cellulose, hydroxypropyl starch, carboxymethyl cellulose calcium, ion exchange resin, methyl cellulose, gelatin, gum arabic, hydroxypropylcellulose, hydroxypropyl methylcellulose, polyvinylpyrrolidone, PVA, light anhydrous silicic acid, magnesium stearate, talc, tragacanth, bentonite, veegum, titanium oxide, fatty acid sorbitan ester, sodium lauryl sulfate, glycerin, fatty acid glycerin ester, purified lanolin, glycerogelatin, polysorbate, Macrogol, vegetable oil, wax, liquid paraffin, white petrolatum, fluorocarbon, nonionic surfactant, propylene glycol, water, benzalkonium chloride, hydrochloric acid, sodium chloride, sodium hydroxide, lactic acid, sodium, sodium monohydrogen phosphate, sodium dihydrogen phosphate, citric acid, sodium citrate, disodium edetate, Poloxamer 407 and polycarbophil. For example, the pharmaceutical composition may contain one or more additives for preparations selected from POE-POP glycol, PVA, hydroxypropyl methylcellulose and methyl cellulose.

The aqueous suspension or pharmaceutical composition can be in the form of a kit, accompanying an outer package, a container, a diluent, a suspension, and/or an instruction for a preparation/administration. When the aqueous suspension or pharmaceutical composition is provided in the form of a kit, different components of the aqueous suspension or pharmaceutical composition may be individually packed in separate containers and contained in a single kit. Alternatively, more than one but not all of the components of the aqueous suspension or pharmaceutical composition may be included in the kit (at least the glucocorticosteroid compound nanoparticles is included in the kit), and other components may be provided separately from the kit. When the aqueous suspension or pharmaceutical composition is provided in the form of a kit, the necessary components are preferably mixed immediately before use to obtain the aqueous suspension or pharmaceutical composition of the present invention.

The kit of the present invention, for example, can be as follows:
(a) a kit for preparing a pharmaceutical composition comprising an aqueous suspension containing nanoparticles of a glucocorticosteroid compound;
(b) the kit of (a) further comprising a dispersion stabilizer;
(c) the kit of (b), wherein the dispersion stabilizer is one or more substances selected from POE-POP glycol, PVA, hydroxypropyl methylcellulose, and methyl cellulose;
(d) the kit of any one of (a) to (c), for preparing a pharmaceutical composition for parenteral administration;
(e) the kit of any one of (a) to (d), for preparing an injection or a topical preparation;
(f) the kit of (e), for preparing a topical eye preparation, a topical ear preparation, a topical nose preparation or a topical lung preparation, or an eye drop, an ear drop, a nose drop or an inhaler;
(g) The kit of any one of (a) to (f), wherein the pharmaceutical composition is a therapeutic drug or a preventive drug for an inflammatory or infectious disease of the eye, ear, nose or lung.

In one embodiment, the present invention may be the method for preparing an aqueous pharmaceutical composition containing the glucocorticosteroid compound nanoparticles, comprising mixing a diluent and the aqueous suspension containing the glucocorticosteroid compound nanoparticles.

In preparing the pharmaceutical composition (e.g., injections, topical eye preparations (preferably eye drops), topical ear preparations (preferably ear drops), topical nose preparations (preferably nose drops) or topical lung preparations (preferably inhalers)), the pH and osmotic pressure are not limited as long as they are acceptable for the topical preparations, and preferably is pH 5 to 9.5, more preferably is pH 6 to 9, further preferably is pH 7 to 9. The ratio of osmotic pressure of the preparation (except ointments) to saline is, for example, about 0.3 to 4.3, preferably about 0.3 to 2.2, particularly preferably about 0.5 to 1.5. The pH and osmotic pressure can be controlled using a pH control agent, a tonicity agent or salts by a method known in the art.

The pharmaceutical composition can be suitably produced by a known method, for example, by mixing the aqueous suspension containing the glucocorticosteroid compound nanoparticles with desired components in a suitable diluent such as distilled water or purified water, adjusting the above osmotic pressure and pH, subjecting to high pressure steam sterilization or filter-sterilization under aseptic conditions, and filling aseptically in a washed sterilized container.

The pharmaceutical composition can be a therapeutic or preventive agent for inflammatory or infectious diseases. For example, the pharmaceutical composition can be a therapeutic or preventive agent for inflammatory or infectious diseases caused by infections. The present invention encompasses the aqueous suspension containing the glucocorticosteroid compound nanoparticles and a dispersion stabilizer for the use as a pharmaceutical (a therapeutic or preventive drug for inflammatory or infectious diseases).

The inflammatory or infectious disease herein encompasses systemic inflammatory and infectious diseases and topical inflammatory and infectious diseases. The inflammatory diseases include, in addition to the inflammatory diseases caused by infections, allergic inflammatory diseases (e.g., allergic rhinitis, allergic conjunctivitis, allergic dermatitis, allergic eczema, allergic asthma and allergic pneumonia). Examples of the systemic inflammatory disease include systemic inflammatory or infectious diseases such as superficial/deep skin infections, lymphangitis/lymphadenitis, mastitis, osteomyelitis, tonsillitis, pneumonia, pyelonephritis, urethritis, gonococcal infection, syphilis, intrauterine infection, scarlet fever, diphtheria, whooping cough, secondary infections from external wounds/burns and surgeries, pharyngitis/laryngitis, bronchitis, secondary infections from chronic respiratory diseases, pericoronitis, periodontal inflammation, tetanus, cystitis, prostatitis, infectious enteritis, jaw inflammation, infectious arthritis and gastritis.

The pharmaceutical composition can be specifically used for treating or preventing eye inflammatory and infectious diseases and various symptoms associated therewith. Examples of the eye inflammatory and infectious disease include eye lid symptoms such as blepharitis, blepharoconjunctivitis, meibomitis, acute or chronic stye, chalazion, dacryocystitis, dacryoadenitis and acne rosacea; conjunctival symptoms such as conjunctivitis, ophthalmia neonatorum and trachoma; corneal symptoms such as corneal ulcer, superficial keratitis and interstitial keratitis, ketatoconjunctivitis, foreign objects and post-surgery infections; and anterior chamber and uvea symptoms such as endophthalmitis, infectious uveitis and post-surgery infections. The prevention of infections includes the administration before surgical treatment such as an operation or before contacting a person presenting infectious symptoms. In using for the prevention, an administration can be before surgical treatments such as blepharoplasty, chalazion removal, blepharorrhaphy, surgeries for canaliculi and lacrimal drainage system and other surgical treatments relating to eyelids and lacrimal apparatus; conjunctival surgeries such as removal of pterygium, pinguecula or tumors, conjunctival transplant, external wounds such as cuts, burns and scratches and conjunctival flap surgery; corneal surgeries such as removal of foreign objects, keratotomy and corneal transplant; refractive surgeries such as photorefractive procedure; glaucoma surgeries such as bleb filtration; anterior chamber paracentesis; iridotomy; cataract surgery; retinal surgery; and extraocular muscle relating surgeries. The prevention of ophthalmia neonatorum is also included in the prevention defined herein.

The pharmaceutical composition of the present invention, for example, can be used for treating or preventing various symptoms associated with inflammatory or infectious diseases of the ear. Examples of the inflammatory or infectious disease of the ear include otitis media and otitis externa. The prevention of infectious diseases includes presurgical treatments and treatments given before conditions of possible infections (e.g., contacts with a person infected or possibly infected). Examples of the prevention include an administration given before surgical treatments associated with external wounds or damages of the ear and other surgeries or treatments.

The pharmaceutical composition further can treat or prevent various symptoms associated with inflammatory or infectious diseases of the nose. Throughout the entire specification, the term "nose" used in the phrases of "inflammatory or infectious diseases of the nose" and the "topical nose preparation" means the entire upper respiratory tract, for example, the nasal cavity, nasopharynx, pharynx and larynx. Examples of the inflammatory or infectious disease of the nose include sinusitis, allergic rhinitis and rhinitis.

The pharmaceutical composition can further be used to treat or prevent various symptoms associated with inflammatory or infectious diseases of the lung. Throughout the entire specification, the term "lung" used in the phrases of "inflammatory or infectious diseases of the lung" and the "topical lung preparation" means the entire lower respiratory tract, for example, the trachea, bronchus, bronchiole and lung. Examples of the inflammatory or infectious diseases of the lung include pneumonia, bronchitis, allergic pneumonia and asthma.

More preferably, the pharmaceutical composition can be used to treat or prevent infectious diseases (e.g., infectious diseases of the eye, ear, nose or lung) caused by various bacteria or parasite. Examples of such microorganism include the *Staphylococcus* genus such as *Staphylococcus aureus* and *Staphylococcus epidermidis*; the *Streptococcus* genus such as *Streptococcus pneumoniae* and *Streptococcus pyogenes*, Groups C, F and G Streptococci and Group viridans *Streptococcus*; *Haemophilus influenzae* including biotype III; *Haemophilus ducreyi*; *Moraxella catarrhalis*; the *Neisseria* genus such as *Neisseria gonorrhoeae* and *Neisseria meningitidis*; the *Chlamydia* genus such as *Chlamydia trachomatis, Chlamydia psittaci* and *Chlamydia pneumoniae*; the *Mycobacterium* genus such as atypical mycobacteria including *Mycobacterium tuberculosis* and *Mycobacterium tubercule bacillus* intracellular complex and *Mycobacterium marinum, Mycobacterium fortuitum* and *Mycobacterium chelonae; Bordetella pertussis; Campylobacter jejuni; Legionella pneumophila; Bacteroides bivius*; Welch *bacillus; Peptostreptococcus* species; *Borrelia burgdorferi; Mycoplasma* pneumonia; *Treponema pallidum; Ureaplasma urealyticum; Toxoplasma*; Malaria; and nosema.

3. Treatment Method/Prevention Method

The pharmaceutical composition of the present invention can be used to treat or prevent inflammatory or infectious diseases by being administered in an effective amount to a patient in need thereof. The present invention accordingly relates to a method for treatment or prevention of inflammatory or infectious diseases, comprising administering an effective amount of the pharmaceutical composition containing the aqueous suspension containing the glucocorticosteroid compound nanoparticles (and a dispersion stabilizer) to a patient in need thereof. The patient herein includes any animals classified in the mammals including but not limited to human; companion animals such as dogs, cats and rabbits; domestic animals such as cows, pigs, sheep and horses, in which human is preferable.

The dose and number of administration of the pharmaceutical composition are not limited and can be suitably selected at a physician's discretion depending on purpose of prevention of deterioration/progress and/or the purpose of treatment of the disease to be treated, the type of disease, and patient's conditions such as body weight and age. The dose is generally about 0.01 to 1000 mg (on an active component weight basis) a day for an adult, and can be administered once or in several times a day. The administration route is an injection or topical administration, for example, intravenous injections, intramuscular injections or subcutaneous injections, intravenous drips, eye drops, ear drops, nose drops, transdermal administration, transmucosal administration or inhalation. The content of the effective agent in the pharmaceutical composition can be, for example, 0.001% to 10%, 0.01% to 1% or 0.05% to 0.1%.

When the pharmaceutical composition of the present invention is in the form of an injection, it can be administered continuously or intermittently in a daily dose of 0.001 to 100 mg (on an active component weight basis) for an adult.

When the aqueous pharmaceutical composition of the present invention is for topical administration, it is directly administered to a topical area such as an affected site, an area around an affected site, or an organ including an affected site. The pharmaceutical composition of the present invention, for example, can be formed into a topical eye preparation, a topical ear preparation, a topical nose preparation or a topical lung preparation. When the pharmaceutical composition of the present invention is a topically administrable preparation, it is applicable every day or in any number of times after a topical inflammatory or infectious disease is developed. The application amount can be suitably determined depending on conditions, and is typically applied to the eye once to six times a day, for example, once, twice, three times, four times, five times or six times a day, with about 1 to 3 drops per application. The administration period can be any period of time until symptoms subside adequately, for example, two weeks to one year.

The present invention is illustrated in more detail below in examples, but which does not intend to limit the scope of the present invention. All of the documents cited throughout this application are incorporated herein by reference in their entirety.

(Example 1) Study on Pulverization of Clobetasol Propionate

In order to examine an effect of anhydrous citric acid and hydrogenated soybean lecithin on pulverization of clobetasol propionate, the following pulverizations (1) to (9) were conducted and the mean particle diameter (Dv), the median particle diameter (D50) and the 90% particle diameter (D90) of the obtained particles were measured using a particle size distribution analyzer (DelsaNano S, Beckman Coulter, Inc.)

(1) Pulverization without Adding Anhydrous Citric Acid or Hydrogenated Soybean Lecithin 10 g of clobetasol propionate (melting point: 193 to 200° C., Tokyo Chemical Industry Co., Ltd.) having a mean particle diameter of 38,390 nm and 110 g of sodium chloride (Tomita Salt K-30, Tomita Pharmaceutical Co., Ltd.) were charged into a 1.0 L water-cooling vertical kneader (INOUE MFG., INC.) and homogeneously mixed. To the mixture, 17 g of glycerin (Sigma-Aldrich Co. LLC.) was added with keeping the mixture in form of dough, and pulverized at 5° C. for 6 hours. Subsequently, 0.1 g of the obtained pulverized-kneaded product (dough) and 5 g of 0.1% POE-POP glycol (UNILUB 70DP-950B, NOF CORPORATION) as the dispersant were weighed into a 50 mL screw bottle, which was dispersed homogeneously using a ultrasonic device (MODEL VS-100III, AS ONE Corporation), and added 45 g of purified water to obtain 50 g of a suspension. The obtained suspension was measured for the particle size distributions using a particle size distribution analyzer (DelsaNano S, Beckman Coulter, Inc.). The particle size distributions of clobetasol propionate were measured to have a mean particle diameter (Dv) of 285 nm, a median particle diameter (D50) of 231 nm and the 90% particle diameter (D90) of 433 nm.

(2) Pulverization with Addition of Anhydrous Citric Acid

Except for adding 0.8 g of anhydrous citric acid (JUNSEI CHEMICAL CO., LTD.) to the mixture, the pulverization was conducted in the same manner as Example 1 (1) at 5° C. for 7 hours. Subsequently, the pulverized-kneaded product (dough) was dispersed in the same manner as Example 1. The clobetasol propionate was measured for the particle size distributions, which showed a mean particle diameter (Dv) of 260 nm, a median particle diameter (D50) of 222 nm and a 90% particle diameter (D90) of 363 nm.

(3) Pulverization with Addition of Hydrogenated Soybean Lecithin

Except for adding 10 g of hydrogenated soybean lecithin (Phospholipon 90H, Lipoid GmbH) to the mixture, the pulverization and subsequent dispersion were conducted in the same manner as Example 1 (1). The particle size distributions of clobetasol propionate were measured to have a mean particle diameter (Dv) of 147 nm, a median particle diameter (D50) of 124 nm and a 90% particle diameter (D90) of 210 nm.

(4) Pulverization with Addition of Anhydrous Citric Acid and Hydrogenated Soybean Lecithin 1

Except for adding 0.8 g of anhydrous citric acid (JUNSEI CHEMICAL CO., LTD.) and 5 g of hydrogenated soybean lecithin (Phospholipon 90H, Lipoid GmbH) to the mixture, the pulverization and subsequent dispersion were conducted in the same manner as Example 1 (1). The particle size distributions of clobetasol propionate were measured to have a mean particle diameter (Dv) of 166 nm, a median particle diameter (D50) of 138 nm and a 90% particle diameter (D90) of 241 nm.

(5) Pulverization with Addition of Anhydrous Citric Acid and Hydrogenated Soybean Lecithin 2

Except for adding 0.8 g of anhydrous citric acid (JUNSEI CHEMICAL CO., LTD.) and 10 g of hydrogenated soybean lecithin (Phospholipon 90H, Lipoid GmbH) to the mixture, the pulverization was conducted in the same manner as Example 1 (1) at 5° C. for 7 hours. Subsequently, the pulverized-kneaded product (dough) was dispersed in the same manner as Example 1. The clobetasol propionate was measured for the particle size distributions, which showed a mean particle diameter (Dv) of 101 nm, a median particle diameter (D50) of 87 nm and a 90% particle diameter (D90) of 141 nm.

(6) Pulverization with Addition of Anhydrous Citric Acid and Hydrogenated Soybean Lecithin 3

Except for adding 0.8 g of anhydrous citric acid (JUNSEI CHEMICAL CO., LTD.) and 20 g of hydrogenated soybean lecithin (Phospholipon 90H, Lipoid GmbH) to the mixture, the pulverization was conducted in the same manner as Example 1 (1) at 5° C. for 7 hours. Subsequently, the pulverized-kneaded product (dough) was dispersed in the same manner as Example 1. The clobetasol propionate was measured for the particle size distributions, which showed a mean particle diameter (Dv) of 144 nm, a median particle diameter (D50) of 121 nm and a 90% particle diameter (D90) of 214 nm.

(7) Pulverization with Addition of Anhydrous Citric Acid and Hydrogenated Soybean Lecithin 4

Except for adding 2 g of anhydrous citric acid (JUNSEI CHEMICAL CO., LTD.) and 5 g of hydrogenated soybean lecithin (Phospholipon 90H, Lipoid GmbH) to the mixture, the pulverization was conducted in the same manner as Example 1 (1) at 5° C. for 7 hours. Subsequently, 0.1 g of the obtained pulverized-kneaded product (dough) and 5 g of 0.01% POE-POP glycol (UNILUB 70DP-950B, NOF CORPORATION) as the dispersant were weighed into a 50 mL screw bottle, and dispersed homogeneously using a ultrasonic device (MODEL VS-100III, AS ONE Corporation), to which 15 g of purified water was added to obtain 20 g of a suspension. The obtained suspension was measured for the particle size distributions using a particle size distribution analyzer (DelsaNano S, Beckman Coulter, Inc.). The particle size distributions of clobetasol propionate were found to have a mean particle diameter (Dv) of 137 nm, a median particle diameter (D50) of 112 nm and a 90% particle diameter (D90) of 209 nm.

(8) Pulverization with Addition of Anhydrous Citric Acid and Hydrogenated Soybean Lecithin 5

Except for adding 2 g of anhydrous citric acid (JUNSEI CHEMICAL CO., LTD.) and 10 g of hydrogenated soybean lecithin (Phospholipon 90H, Lipoid GmbH) to the mixture, the pulverization was conducted in the same manner as Example 1 (1) at 5° C. for 6 hours. Subsequently, 0.1 g of the obtained pulverized-kneaded product (dough) was dispersed in the same manner as Example 1 (1). The obtained suspension was measured for the particle size distributions. The particle size distributions of clobetasol propionate were found to have a mean particle diameter (Dv) of 129 nm, a median particle diameter (D50) of 112 nm and a 90% particle diameter (D90) of 179 nm.

(9) Pulverization with Addition of Anhydrous Citric Acid and Hydrogenated Soybean Lecithin 6

Except for adding 2 g of anhydrous citric acid (JUNSEI CHEMICAL CO., LTD.) and 20 g of hydrogenated soybean lecithin (Phospholipon 90H, Lipoid GmbH) to the mixture, the pulverization was conducted in the same manner as in Example 1 (1) at 5° C. for 7 hours. Subsequently, 0.1 g of the obtained pulverized-kneaded product (dough) was dispersed in the same manner as Example 1 (1). The obtained suspension was measured for the particle size distributions. The particle size distributions of clobetasol propionate were found to have a mean particle diameter (Dv) of 147 nm, a median particle diameter (D50) of 121 nm and a 90% particle diameter (D90) of 228 nm.

Table 1 shows the conditions of pulverization (1) to (9) and the particle diameters obtained as the result of pulverizations. This results suggest that the pulverization formulation (5) showed the best pulverization performance.

[Table 1]

(Example 2) Study on Formulation of Clobetasol Propionate (1) Study on the Dispersant 0.1 g of the pulverized-kneaded product (dough) obtained in Example 1 (4) and 5 g of an aqueous solution containing each dispersant shown in Table 2 were weighed into a 50 mL screw bottle, and dispersed homogeneously using a ultrasonic device (MODEL VS-100III, AS ONE Corporation), to which 45 g of purified water was added to obtain 50 g of a dispersion. Each of the obtained dispersions was stored at room temperature (about 25° C.) for 1 day. The transparency and the presence of precipitation were visually observed immediately after the dispersion and after 1 day storage to evaluate the stability of dispersions.

The results are shown in Table 2. The symbols used in Table 2 to describe the evaluated storage stability mean as follows. Good: good stability, Fair: stable immediately after dispersion but precipitation was generated as time advances; Poor: unstable, turbidity was identified immediately after preparation. The test results shown in Table 2 revealed that the suspension using POE-POP glycol (PLONON 407P, Pluronic F68, UNILUB 70DP-950B) and PVA (Kuraray POVAL 217C) as the dispersant exhibited no precipitation detected and the transparency maintained with good stability at both of immediately after dispersion and even after 1 day storage.

[Table 2]
(2) Study on the Thickener 0.1 g of the pulverized-kneaded product (dough) obtained in Example 1 (4) and 7.3 g of an aqueous solution of mixture of 0.1% Pluronic F68/0.01% Tween80 (1:1) were weighed into a 50 mL screw bottle, and dispersed homogeneously for 3 minutes using a ultrasonic homogenizer (Sonicator S-4000, #418 microtip, power output 30, Astrason), to which 1.5 g of the aqueous solution containing each of the thickeners shown in Table 3 was added and subsequently 13.5 g of purified water was added to obtain 22.4 g of a dispersion. The final concentration of each thickener was as shown in Table 3. Each of the obtained dispersions was stored at room temperature (about 25° C.) for 4 days and the transparency and the presence of precipitation was visually observed to evaluate the stability.

The results are shown in Table 3. The symbols used in Table 3 to describe the evaluated storage stability mean as follows. Good: good stability; Fair: stability is low, modest precipitation was found; Poor: unstable, full precipitation was observed. The test results shown in Table 3 revealed that the suspension using hydroxypropyl methylcellulose and methylcellulose as the thickener exhibited no precipitation detected and the transparency maintained with good stability at both of immediately after dispersion and even after 4 days storage.

[Table 3]
(3) Study on the Preservative 1

0.1 g of the pulverized-kneaded product (dough) obtained in Example 1 (4), 7.3 g of an aqueous solution of mixture of 0.1% Pluronic F68/0.01% Tween80 (1:1), and 1.43 g of a 1% Kurary POVAL 217C aqueous solution were weighed into a 50 mL screw bottle, and dispersed homogeneously for 7 minutes using a ultrasonic homogenizer (Sonicator S-4000, #418 microtip, power output 30, Astrason), to which 1.43 g of a 0.01% benzalkonium chloride aqueous solution and 1.43 g of a 3% TC-5(R) aqueous solution were added. To thus obtained mixture, a 100 mM sodium citrate aqueous solution was gradually added with stirring up to pH 7.0, to which purified water was added to obtain 14.6 g of an eye drop. The obtained eye drop was stored at a cycle of 5° C.-25° C. or at 40° C. for 7 days and the transparency was visually observed to evaluate the stability.

The results of Example 2 (3) are shown in Table 4. The "cycle (5° C.-25° C.)" in the storage temperature in Table 4 means that the eye drop was stored repeatedly at 5° C. for 6 hours and then at 25° C. for 6 hours. The test results shown in Table 4 revealed that the eye drop prepared using benzalkonium chloride as the preservative maintained the transparency and had good stability at both of immediately after preparation and even after 7 days storage.

[Table 4]

(Example 3) Study on the Filter-Sterilization (1) Preparation of an Eye Drop 1

6.0 g of the pulverized-kneaded product (dough) obtained in Example 1 (5), 408 g of a 0.01% UNILUB 70DP-950B aqueous solution, and 81.6 g of a 1.0% Kurary POVAL 217C aqueous solution were added to a 1 L-beaker, roughly dispersed using a ultrasonic device (MODEL VS-100III, AS ONE Corporation), and then uniformly dispersed using a high pressure homogenizer (L01-YH1, 90 MPa×5 passes, SANWA ENGINEERING LTD.). To the obtained mixture, 7.48 g of a 0.1% benzalkonium chloride aqueous solution and 7.48 g of a 3% TC-5 (R) aqueous solution were added, which was stirred for 5 minutes. A 100 mM sodium citrate aqueous solution was added thereto up to pH 7.0, to which purified water was added with stirring to give the total amount of 748 g. The obtained eye drop was measured for the particle size distributions using a particle size distribution analyzer (DelsaNano S, Beckman Coulter, Inc.), which showed to have a mean particle diameter (Dv) of 173 nm, a median particle diameter (D50) of 151 nm and a 90% particle diameter (D90) of 233 nm.

(2) Preparation of an Eye Drop 2

6.0 g of the pulverized-kneaded product (dough) obtained in Example 1 (7), 414 g of a 0.01% UNILUB 70DP-950B aqueous solution, and 82.8 g of a 1.0% Kurary POVAL 217C aqueous solution were added to a 1 L-beaker, roughly dispersed using a ultrasonic device (MODEL VS-100III, AS ONE Corporation), and then uniformly dispersed using a high pressure homogenizer (L01-YH1, 90 MPa×5 passes, SANWA ENGINEERING LTD.). To the obtained mixture, 7.5 g of a 0.1% benzalkonium chloride aqueous solution and 7.5 g of a 3% TC-5 (R) aqueous solution were added, and stirred for 5 minutes. A 100 mM sodium citrate aqueous solution was added thereto up to pH 7.0, to which purified water was added with stirring to give a total amount of 750 g. The obtained eye drop was measured for the particle size distributions using a particle size distribution analyzer (DelsaNano S, Beckman Coulter, Inc.) which showed a mean particle diameter (Dv) of 201 nm, a median particle diameter (D50) of 177 nm and a 90% particle diameter (D90) of 260 nm.

(3) Preparation of an Eye Drop 3

To a 1 L-beaker, 6.29 g of the pulverized-kneaded product (dough) obtained in Example 1 (8), 415 g of a 0.01% UNILUB 70DP-950B aqueous solution, and 83.0 g of a 1.0% Kurary POVAL 217C aqueous solution were added, and roughly dispersed using a ultrasonic device (MODEL VS-100III, AS ONE Corporation), which was then uniformly dispersed using a high pressure homogenizer (L01-YH1, 90 MPa×5 passes, SANWA ENGINEERING LTD.). To the mixture, 7.84 g of a 0.1% benzalkonium chloride aqueous solution and 7.84 g of a 3% TC-5 (R) aqueous solution were added, and the mixture was stirred for 5 minutes. The pH of the mixture was adjusted with 100 mM sodium citrate aqueous solution up to pH 7.0. Then purified water was added with stirring to give the total amount of 784 g. The obtained eye drop was measured for the particle size distributions using a particle size distribution analyzer (DelsaNano S, Beckman Coulter, Inc.), which showed a mean particle diameter (Dv) of 204 nm, a median particle diameter (D50) of 166 nm and a 90% particle diameter (D90) of 306 nm.

(4) Study on the Filtration Permeability

Each of the eye drops prepared in Examples 3 (1) to (3) was tested for the filtration permeability using two types of filter membranes (Optiscale 25 and Optiscale 25 Capsule) manufactured by Merck Millipore Corporation. Filtration conditions were as follows.

Filter Names:
Optiscale 25 (pre-filter 0.5 μm/main filter 0.22 μm)
Optiscale 25 Capsule (pre-filter 0.2 μm/main filter 0.22 μm)
Filter material: polyvinylidene fluoride (PVDF)
Effective filtration area: 3.5 cm$^2$
Test pressure: 0.18 MPa The test was conducted by the Vmax method which measures a permeation flow rate of the eye drop over time to estimate the maximum processing amount of the filter, and the filtration was not continued until the filter completely clogs.

The results are shown in Table 5. The permeation amount shown in Table 5 represents the converted value of permeated amount of each eye drop through the filter to L/m². The permeation ratio is a percentage of the post-filtration concentration relative to the pre-filtration concentration, in which the pre- and post-filtration concentrations of clobetasol propionate were measured by HPLC. The results shown in Table 5 revealed that all of the particle diameters can be sterilized by filtration. The eye drop prepared in Example 3 (1) containing the smallest particle diameter of the clobetasol propionate after pulverization showed the highest values in both permeation amount and permeation ratio.

[Table 5]

(Example 4) Pulverization of Clobetasol Propionate (1) Production of Nanoparticles with a Mean Particle Diameter of 100 to 150 nm To a 1.0 L water-cooling vertical kneader (INOUE MFG., INC.), 10 g of clobetasol propionate (melting point: 193 to 200° C., Tokyo Chemical Industry Co., Ltd.) having a mean particle diameter of 38,390 nm, 110 g of sodium chloride (Tomita Salt K-30, Tomita Pharmaceutical Co., Ltd.), 10 g of hydrogenated soybean lecithin (Phospholipon 90H, Lipoid GmbH) and 0.8 g of anhydrous citric acid (JUNSEI CHEMICAL CO., LTD.) were charged, and homogeneously mixed. To the mixture, 17 g of glycerin (Sigma-Aldrich Co. LLC.) was added with keeping the mixture in a state of dough, and pulverized at 5° C. for 7 hours. Subsequently, 0.1 g of the obtained pulverized-kneaded product (dough) and 5 g of 0.01% POE-POP glycol (UNILUB 70DP-950B, NOF CORPORATION) as the dispersant were weighed into a 50 mL screw bottle, which were dispersed homogeneously using a ultrasonic device (MODEL VS-100III, AS ONE Corporation), and 45 g of purified water was added thereto to obtain 50 g of a suspension. The obtained suspension was measured for the particle size distributions using a particle size distribution analyzer (DelsaNano S, Beckman Coulter, Inc.), and the particle size distributions of clobetasol propionate were found to have a mean particle diameter (Dv) of 101 nm, a 10% particle diameter (D10) of 56 nm, a median particle diameter (D50) of 87 nm and a 90% particle diameter (D90) of 141 nm.

(2) Production of Nanoparticles with a Mean Particle Diameter of 100 to 150 nm

Clobetasol propionate was pulverized and measured for the particle size distributions in the same manner as (1). The particle size distributions of clobetasol propionate were found to have a mean particle diameter (Dv) of 108 nm, a 10% particle diameter (D10) of 57 nm, a median particle diameter (D50) of 89 nm and a 90% particle diameter (D90) of 151 nm.

(3) Production of Nanoparticles with a Mean Particle Diameter of 250 to 300 nm

Clobetasol propionate was pulverized and measured for the particle size distributions in the same manner as (1), except for no addition of 10 g of hydrogenated soybean lecithin (Phospholipon 90H, Lipoid GmbH). The particle size distributions of clobetasol propionate were found to have a mean particle diameter (Dv) of 260 nm, a 10% particle diameter (D10) of 143 nm, a median particle diameter (D50) of 222 nm and a 90% particle diameter (D90) of 363 nm.

(4) Production of Nanoparticles with a Mean Particle Diameter of 500 to 700 nm

Into the Mortar Grinder RM 200 (Retsch GmbH), 1 g of clobetasol propionate having a mean particle diameter of 38,390 nm and 2 g of a mixture of sodium chloride and glycerin (sodium chloride 11 g, glycerin 2 g) were charged and pulverized repeatedly nine times for 1 minute per operation at room temperature. Subsequently, 0.04 g of the obtained pulverized-kneaded product (dough) and 5 g of 0.01% POE-POP glycol (UNILUB 70DP-950B) as the dispersant were weighed into a 50 mL screw bottle, which was dispersed homogeneously using a ultrasonic device. To the dispersed mixture, 45 g of purified water was added to obtain 50 g of a suspension. The obtained suspension was measured for the particle size distributions using a particle size distribution analyzer, and the particle size distributions of clobetasol propionate were found to have a mean particle diameter (Dv) of 637 nm, a 10% particle diameter (D10) of 233 nm, a median particle diameter (D50) 475 nm and a 90% particle diameter (D90) of 1129 nm.

(Example 5) Preparation of an Ophthalmic Suspension Containing Clobetasol Propionate Nanoparticle (1) Preparation of a 0.05% Ophthalmic Nanoparticle Suspension (a Mean Particle Diameter of about 100 nm)

Into a beaker, 2.4 g of the pulverized-kneaded product (dough) produced in Example 4 (1), 150 g of a 0.01% UNILUB aqueous solution and 30 g of a 1.0% PVA (Merck KGaA) aqueous solution were weighed, and homogeneously dispersed for about 5 minutes using a ultrasonic device (MODEL VS-100III, AS ONE Corporation) to give a crude dispersion, which was processed using a high pressure homogenizer (SANWA ENGINEERING LTD., L01-YH1) to obtain a dispersion. To the dispersion, 2.5 g of a 0.1% benzalkonium chloride (BAC) aqueous solution and 2.5 g of a 3.0% hydroxypropyl methylcellulose (HPMC) aqueous solution were added, to which subsequently a 500 mM sodium citrate was gradually added up to pH 7.0. Water for injection was then added thereto to give a total amount of 417.6 g to obtain a 0.05% ophthalmic nanosuspension (a mean particle diameter of about 100 nm). The obtained ophthalmic suspension had an osmotic pressure ratio of 0.8.

(2) Preparation of a 0.05% Ophthalmic Nanosuspension (a Mean Particle Diameter of about 300 nm)

Into a beaker, 2.1 g of the pulverized-kneaded product (dough) produced in Example 4 (3), 150 g of a 0.01% UNILUB aqueous solution and 30 g of a 1.0% PVA aqueous solution were weighed, and homogeneously dispersed for about 5 minutes using a ultrasonic device (MODEL VS-100III, AS ONE Corporation) to give a crude dispersion, which was processed using a high pressure homogenizer (SANWA ENGINEERING LTD., L01-YH1) to obtain a dispersion. To the dispersion, 2.5 g of a 0.1% BAC aqueous solution and 2.5 g of a 3.0% HPMC aqueous solution were added, to which subsequently a 500 mM sodium citrate was gradually added up to pH 7.0. Water for injection was then added to give a total amount of 405.4 g to obtain a 0.05% ophthalmic nanosuspension (a mean particle diameter of about 300 nm). The obtained ophthalmic suspension had an osmotic pressure ratio of 0.8.

(3) Preparation of a 0.05% Ophthalmic Nanosuspension (a Mean Particle Diameter of about 600 nm)

Into a beaker, 0.52 g of the pulverized-kneaded product (dough) produced in Example 4 (4), 150 g of water for injection and 30 g of a 1.0% PVA aqueous solution were weighed, and homogeneously dispersed for about 5 minutes using a ultrasonic device (MODEL VS-100III, AS ONE Corporation) to give a crude dispersion, which was processed using a high pressure homogenizer (SANWA ENGI- NEERING LTD., L01-YH1) to obtain a dispersion. To the dispersion, 2.5 g of a 0.1% BAC aqueous solution and 2.5 g of a 3.0% HPMC aqueous solution were added, to which subsequently a 500 mM sodium citrate was gradually added up to pH 7.0. To the obtained mixture, 1.45 g of sodium chloride was added, and then water for injection was added to give a total amount of 245 g to obtain a 0.05% ophthalmic nanosuspension (a mean particle diameter of about 600 nm). The obtained ophthalmic suspension had an osmotic pressure ratio of 0.9.

Table 6 shows the composition of each of the 0.05% clobetasol propionate ophthalmic nanosuspensions prepared in Examples 5 (1) to (3).
[Table 6]

(Example 6) Intraocular Pharmacokinetics Test

The ophthalmic nanosuspensions prepared in Examples 5(1) to 5(3) were ophthalmically administered into the eyes of rabbits (Kbl:JW, male) to test an intraocular pharmacokinetics (n=3). The lower eyelid of each rabbit was gently pulled off, the test substance was ophthalmically administered into the conjunctival sac of the left eye using a pipette (single ocular administration, 50 μL/eye), and the upper and lower eyelids were gently closed after administration and held for about 2 seconds. After 15 minutes, 30 minutes, 60 minutes, and 90 minutes from the administration, the rabbits were anesthetized by administering an aqueous solution of pentobarbital sodium (Tokyo Chemical Industry Co., Ltd.) via their auricular veins and then euthanized by bleeding. Eyes were thoroughly washed with water for injection, the aqueous humor (left eye) was collected, and subsequently the conjunctiva (left eye) was collected. Each of the collected aqueous humor and conjunctiva was weighed by an electronic force balance, and then frozen by liquid nitrogen, which was stored in an ultracold freezer (acceptable range: −70° C. or lower) until measurement. The clobetasol propionate concentrations in aqueous humor and conjunctiva were measured by LC-MS/MS.
(Pretreatment of Aqueous Humor)

To 25 μL of the collected aqueous humor, 20 μL of methanol and 20 μL of a solution of an internal standard substance (prednisolone) were added and thoroughly stirred. To the resulting mixture, 100 μL of acetonitrile was added and thoroughly stirred. After centrifugation (13100×g, 4° C., 5 minutes), 10 μL of the supernatant was injected into the LC-MS/MS.
(Pretreatment of Conjunctiva)

To the collected conjunctiva, ultrapure water was added in a nine times volume of the wet weight of the conjunctiva, and homogenized. To 25 μL of the homogenate, 25 μL of methanol and 20 μL of a solution of an internal standard substance (prednisolone) were added, and thoroughly stirred. To the resulting mixture, 100 μL of acetonitrile was added, and thoroughly stirred. After centrifugation (13100× g, 4° C., 5 minutes), 20 μL of the supernatant was injected into the LC-MS/MS.
(Measurement Conditions in LC-MS/MS)
(Measurement Conditions in HPLC)
Column: CAPCELL PAK C18 MGIII (5 μm, 2 mm×150 mm, Shiseido Company, Limited)
Mobile Phase A: 0.2% aqueous solution of formic acid
Mobile Phase B: Acetonitrile
Gradient Time Program: The following volume ratios were employed.

| Time (min) | Mobile Phase A (%) | Mobile Phase B (%) |
| --- | --- | --- |
| 0.00 | 70 | 30 |
| 2.20 | 70 | 30 |
| 2.50 | 20 | 80 |
| 5.40 | 20 | 80 |
| 5.41 | 70 | 30 |
| 7.00 | 70 | 30 |

Flow Rate: 0.3 mL/min
Column Temperature: 40° C.
Autosampler Temperature: 4° C.
Analysis Time: 7 minutes
(Measurement Conditions in MS/MS)
Ion Source: Electrospray ionization (ESI)
Scan Type: Multiple reaction monitoring (MRM)
Polarity: Positive
Source Temperature: 400° C.
Monitored Ions:

| Compounds | Q1 (m/z) | Q3 (m/z) |
| --- | --- | --- |
| Clobetasol Propionate | 468.1 | 356.3 |
| Internal Standard Substance (Prednisolone) | 361.3 | 147.1 |

Acceptable Range: Within ±0.5

As the results of the intraocular pharmacokinetics test of the ophthalmic nanosuspensions prepared in Examples 5(1) to 5(3), the time course changes of the drug concentration in aqueous humor are shown in FIG. 1 and Table 7, and the time course changes of the drug concentration in conjunctiva are shown in FIG. 2 and Table 8. The drug concentration in aqueous humor indicated particle diameter dependence. The drug concentration in aqueous humor tends to increase with decreasing particle diameter. Thus, it is shown that a smaller particle diameter is more suitable for achieving better migration of the ophthalmically administered nano-sized clobetasol propionate into aqueous humor. The drug concentration in conjunctiva also showed a trend for particle diameter dependence, which indicated that a smaller particle diameter is more suitable for transferability of the ophthalmically administered nano-sized clobetasol propionate into conjunctiva.
[Table 7]
[Table 8]

(Example 7) Examination of Influence of Thickener on Ophthalmic Nanosuspension

Since Example 6 showed that the mean particle diameter of the nano-sized clobetasol propionate is suitably about 100 nm, using ophthalmic suspensions containing nano-sized clobetasol propionate with a mean particle diameter of about 100 nm, an intraocular pharmacokinetics were tested for various viscosities of ophthalmic nanosuspensions which were controlled by employing various thickeners.
(1) Preparation of Ophthalmic Nanosuspension P Into a beaker, 5 g of the pulverized-kneaded product (dough) produced in Example 4(2), 335 g of a 0.01% aqueous solution of UNILUB, and 67 g of a 1.0% aqueous solution of PVA were weighed, which were homogeneously dispersed for about 5 minutes using an ultrasonic device (MODEL VS-100III, AS ONE Corporation) to give a crude dispersion. The crude dispersion was processed by a high-pressure homogenizer (L01-YH1, SANWA ENGINEERING LTD.) to obtain a dispersion. To the dispersion, 6.7 g of a 0.1% aqueous solution of BAC and 201 g of an aqueous solution of 1.0% HPMC (60SH-50) were added, and then 500 mM sodium citrate was gradually added to adjust the pH to 7.0. Subsequently, water for injection was added to give a total amount of 670 g to obtain a 0.05% ophthalmic nanosuspension P. The viscosity of the ophthalmic suspension was about 2 mPa·S.

(2) Preparation of Ophthalmic Nanosuspension Q

A 0.05% ophthalmic nanosuspension Q was prepared in the same manner as Example 7(1), except for substituting "100.5 g of an aqueous solution of 1.0% HPMC (60SH-4000)" for "201 g of an aqueous solution of 1.0% HPMC (60SH-50)". The viscosity of the ophthalmic suspension was about 3 mPa·S.

(3) Preparation of Ophthalmic Nanosuspension R

A 0.05% ophthalmic nanosuspension R was prepared in the same manner as Example 7(1), except for substituting "134 g of an aqueous solution of 1.0% MC (SM-100)" for "201 g of an aqueous solution of 1.0% HPMC (60SH-50)". The viscosity of the ophthalmic suspension was about 2 mPa·S.

(4) Preparation of Ophthalmic Nanosuspension S

A 0.05% ophthalmic nanosuspension S was prepared in the same manner as Example 7(1), except for substituting "100.5 g of an aqueous solution of 1.0% MC (SM-4000)" for "201 g of an aqueous solution of 1.0% HPMC (60SH-50)". The viscosity of the ophthalmic suspension was about 3 mPa·S.

The compositions of the 0.05% clobetasol propionate ophthalmic nanosuspensions prepared in Examples 7(1) to 7(4) are shown in the following Table 9.
[Table 9]

(5) Intraocular Pharmacokinetics Test

The ophthalmic nanosuspensions prepared in Examples 7(1) to 7(4) were subjected to an intraocular pharmacokinetics test according to the method described in Example 6.

(6) Results

The time course changes of the drug concentration in aqueous humor are shown in FIG. 3 and Table 10, and the time course changes of the drug concentration in conjunctiva are shown in FIG. 4 and Table 11. The results shown in FIG. 3 demonstrated that higher viscosity of an ophthalmic suspension showed better transferability of the ophthalmic suspension into aqueous humor. The results shown in FIG. 4 demonstrated that higher viscosity of an ophthalmic suspension showed better transferability of the ophthalmic suspension into conjunctiva in the initial phase (in the first 15 minutes).
[Table 10]
[Table 11]

(Example 8) Efficacy of Clobetasol Ophthalmic Nanosuspension for Rabbit Model of BSA-Induced Uveitis (1) Pulverization of Clobetasol Propionate Clobetasol propionate was pulverized in the same manner as Example 4(1) to produce a pulverized-kneaded product (dough) containing clobetasol propionate particles with a particle size distribution having the mean particle diameter (Dv) of 132 nm, the 10% particle diameter (D10) of 65 nm, the median particle diameter (D50) of 109 nm, and the 90% particle diameter (D90) of 186 nm.

(2) Preparation of 0.05% Clobetasol Propionate Ophthalmic Nanosuspension

Into a beaker, 2.4 g of the pulverized kneaded product (dough) prepared in (1) above, 167.5 g of a 0.01% aqueous solution of POE.POP glycol, and 33.5 g of a 1.0% aqueous solution of PVA were weighed, and dispersed using an ultrasonic device (MODEL VS-100III, AS ONE Corporation) to give a crude dispersion. The crude dispersion was processed by a high-pressure homogenizer (L01-YH1, SANWA ENGINEERING LTD.) five times to obtain a dough dispersion. To the dispersion, 2.8 g of a 0.1% aqueous solution of benzalkonium chloride and 56.4 g of a 1.0% aqueous solution of methyl cellulose were added, and then a 500 mM aqueous solution of sodium citrate was gradually added to adjust the pH to 7.0. Then, 1.5 g of glycerin was added to adjust the osmotic pressure ratio to 1.0, and water for injection was added to give 282.1 g in a total amount of a 0.05% clobetasol propionate ophthalmic nanosuspension. The composition and physical properties of the ophthalmic suspension are shown in the following tables.

Composition of Ophthalmic Suspension

| Components | Composition (%) |
| --- | --- |
| Clobetasol Propionate | 0.05 |
| Sodium Chloride | 0.50 |
| Hydrogenated Soybean Lecithin | 0.05 |
| Glycerin | 0.08 |
| Anhydrous Citric Acid | 0.004 |
| Polyoxyethylene Polyoxypropylene Glycol | 0.005 |
| Polyvinyl Alcohol | 0.1 |
| Benzalkonium Chloride | 0.001 |
| Methyl Cellulose | 0.20 |
| Sodium Citrate | quantum sufficit |
| Water for Injection | quantum sufficit |

Physical Properties of Ophthalmic Suspension

| Measurement Items | Measured Values |
| --- | --- |
| Clobetasol Propionate Concentration (%) | 0.05 |
| Osmotic Pressure Ratio | 1.0 |
| pH | 7.0 |
| Viscosity (mPa · S) | 2.1 |

(3) Efficacy Using Rabbit Model of BSA-Induced Uveitis

Rabbits (Std:JW/CSK) were anesthetized by a combination of ketamine hydrochloride (500 mg of Ketalar for intramuscular injection) and xylazine (2% Celactal injection), and 0.4% oxybuprocaine hydrochloride (Benoxil ophthalmic solution 0.4%) was ophthalmically administered into the right eyeball of each rabbit to anesthetize. After loss of corneal reflex, 0.1 mL of a 10% physiological saline solution of BSA was injected into the central region of the vitreous body of the right eye to cause uveitis (the first induction). From the next day, 50 μL of a control substance (physiological saline solution), 50 μL of the test substance (the 0.05% clobetasol propionate ophthalmic nanosuspension prepared in (2) above), and 50 μL of a positive control substance (commercially-available 0.1% fluorometholone ophthalmic solution) were each weighed with a micropipette and administered into the right eyeballs twice a day (at 9:00 and 17:00 in principle) for 29 consecutive days. The left eyes were untreated, and n=5 for each group.

During 4 days from the 15th to 18th day after the first administration of BSA, the symptoms of inflammation of the external eye (the outside of the cornea) and the internal eye (the inside of the cornea) were scored according to the ocular inflammation grading criteria specified by Yamauchi et al.

(Hideyasu Yamauchi et al. (1973), Folia ophthalmologica Japonica, 24, 969-979) to evaluate the anti-inflammatory effect. On the 27th day, a physiological saline solution of 1.25% BSA was injected via the auricular veins at a dose of 2 mL/kg to cause uveitis (the second induction). On the 29th day, the symptoms of inflammation of the external and internal eyes were scored in the same manner as described above to evaluate the anti-inflammatory effect.

(4) Results

The results are shown in FIGS. 5 to 7, which demonstrated that the 0.05% clobetasol propionate ophthalmic nanosuspension has the same anti-inflammatory effect on the inflammation model of external and internal eyes as the 0.1% fluorometholone ophthalmic solution.

(Example 9) Efficacy for Rat Model of Croton-Induced Conjunctivitis (1) Preparation of 0.1% Clobetasol Propionate Ophthalmic Nanosuspension Into a beaker, 4.2 g of the pulverized-kneaded product (dough) prepared in Example 8(1) above, 150 g of a 0.01% aqueous solution of polyoxyethylene polyoxypropylene glycol, and 30 g of a 1.0% aqueous solution of PVA were weighed, and were dispersed using an ultrasonic device (MODEL VS-100III, AS ONE Corporation) to give a crude dispersion. The crude dispersion was processed by a high-pressure homogenizer (L01-YH1, SANWA ENGINEERING LTD.) five times to obtain a dough dispersion. To the dispersion, 2.4 g of a 0.1% aqueous solution of benzalkonium chloride and 48.3 g of a 1.0% aqueous solution of methyl cellulose were added, and then a 500 mM aqueous solution of sodium citrate was gradually added to adjust the pH to 7.0. Then, water for injection was added to give 241.4 g in total amount of 0.1% clobetasol propionate ophthalmic nanosuspension. The composition and physical properties of the ophthalmic suspension are shown in the following tables.

Composition of Ophthalmic Suspension

| Components | Composition (%) |
|---|---|
| Clobetasol Propionate | 0.1 |
| Sodium Chloride | 1.1 |
| Hydrogenated Soybean Lecithin | 0.1 |
| Glycerin | 0.16 |
| Anhydrous Citric Acid | 0.008 |
| Polyoxyethylene Polyoxypropylene Glycol | 0.005 |
| Polyvinyl Alcohol | 0.1 |
| Benzalkonium Chloride | 0.001 |
| Methyl Cellulose | 0.20 |
| Sodium Citrate | quantum sufficit |
| Water for Injection | quantum sufficit |

Physical Properties of Ophthalmic Suspension

| Measurement Items | Measured Values |
|---|---|
| Clobetasol Propionate Concentration (%) | 0.1 |
| Osmotic Pressure Ratio | 1.6 |
| pH | 7.0 |
| Viscosity (mPa · S) | 1.9 |

(2) Efficacy Using Rat Model of Croton-Induced Conjunctivitis

Ethanol (inflammatory agent) was ophthalmically administered into both eyes of rats (Wistar, female) at a dose of 2.5 µL/site to cause inflammation at −41 minutes and at 0 minute, twice in total. The test substance (0.1% clobetasol propionate ophthalmic nanosuspension prepared in (1)) and a positive control substance (commercially-available 0.1% dexamethasone) were ophthalmically administered into both eyes of the rats with a micropipette at a dose of 5 µL/site twice, 1 minute before the first administration of the inflammatory agent (at −42 minutes) and 1 minute before the second administration of the inflammatory agent (at −1 minute). A normal control group (not caused inflammation without drug administration) and an inflammation control group (caused inflammation without drug administration) were used as control groups, and n=10 for each group.

A 10% ethanol solution of croton oil (inflammation-inducing agent) was ophthalmically administered into both eyes of the rats at a dose of 5 µL/site to induce inflammation three times in total, 40 minutes after, 100 minutes after, and 160 minutes after the second administration of the inflammatory agent. After 2 hours from the last administration of the 10% ethanol solution of croton oil, the rats were euthanized by cervical dislocation under isoflurane anesthesia, and then the conjunctiva was collected from both eyes. The weight of the conjunctiva was measured. The anti-inflammatory effect of the test substance was evaluated from the conjunctival weight comparing with the conjunctival weight of the inflammation control group.

The results are shown in FIG. 8, which show that the conjunctival weight of the inflammation control group was greater than that of the normal control group, and thus inflammation was confirmed to be induced in the model. The conjunctival weights of both of the groups in which the test substance (0.1% clobetasol propionate ophthalmic nanosuspension) was administered and in which the positive control substance (0.1% dexamethasone) was administered were smaller than that of the inflammation control group. Thus, the 0.1% clobetasol propionate ophthalmic nanosuspension of the present application was shown to be able to suppress edema of the conjunctiva in ophthalmically administering into the eyes of rats model of croton-induced conjunctivitis.

(Example 10) Efficacy for Rat Model of Carrageenan-Induced Conjunctival Edema (1) Preparation of 0.1% Clobetasol Propionate Ophthalmic Nanosuspension Into a beaker, 4.3 g of the pulverized kneaded product (dough) prepared in Example 8(1) above, 150 g of a 0.01% aqueous solution of polyoxyethylene polyoxypropylene glycol, and 30 g of a 1.0% aqueous solution of PVA were weighed, and were dispersed using an ultrasonic device (MODEL VS-100III, AS ONE Corporation) to give a crude dispersion. The crude dispersion was processed by a high-pressure homogenizer (L01-YH1, SANWA ENGINEERING LTD.) five times to obtain a dough dispersion. To the dispersion, 2.4 g of a 0.1% aqueous solution of benzalkonium chloride and 47.9 g of a 1.0% aqueous solution of methyl cellulose were added, and then a 500 mM aqueous solution of sodium citrate was gradually added to adjust the pH to 7.0. Then, water for injection was added to give 239.5 g in a total amount of 0.1% clobetasol propionate ophthalmic nanosuspension. The composition and physical properties of the ophthalmic suspension are shown in the following tables.

Composition of Ophthalmic Suspension

| Components | Composition (%) |
| --- | --- |
| Clobetasol Propionate | 0.1 |
| Sodium Chloride | 1.0 |
| Hydrogenated Soybean Lecithin | 0.1 |
| Glycerin | 0.16 |
| Anhydrous Citric Acid | 0.008 |
| Polyoxyethylene Polyoxypropylene Glycol | 0.005 |
| Polyvinyl Alcohol | 0.1 |
| Benzalkonium Chloride | 0.001 |
| Methyl Cellulose | 0.20 |
| Sodium Citrate | quantum sufficit |
| Water for Injection | quantum sufficit |

Physical Properties of Ophthalmic Suspension

| Measurement Items | Measured Values |
| --- | --- |
| Clobetasol Propionate Concentration (%) | 0.1 |
| Osmotic Pressure Ratio | 1.5 |
| pH | 7.0 |
| Viscosity (mPa · S) | 1.9 |

(2) Efficacy Using Rat Model of Carrageenan-Induced Conjunctival Edema

A control substance (physiological saline solution), the test substances (the 0.05% clobetasol propionate ophthalmic nanosuspension prepared in Example 8(2) and the 0.1% clobetasol propionate ophthalmic nanosuspension prepared in Example 10(1)), and a positive control substance (commercially-available 0.1% fluorometholone ophthalmic solution) were administered into the right eyes of rats (Wistar, male) using a micropipette (n=8 for each group). After 15 minutes from the ophthalmic administration, 50 µL of a physiological saline solution of 1% carrageenan (inflammatory substance) was subcutaneously administered into the right upper palpebral conjunctiva of the rats under isoflurane anesthesia to generate a conjunctival edema model. After 4 hours from the administration of the inflammatory substance, the rats were euthanized by bleeding from abdominal aorta under isoflurane anesthesia, and each edematous area including the right eyeball and accessory lacrimal glands (Harderian glands) was isolated. The right palpebral conjunctiva was then separated from the edematous area, and the weight of the conjunctiva was measured. The determined palpebral conjunctival weights were compared to evaluate the anti-inflammatory effect.

The results of the measurement of the palpebral conjunctival weight are shown in FIG. 9, which demonstrated the concentration dependent anti-inflammatory effect of the clobetasol propionate ophthalmic nanosuspension, and showed that the 0.1% clobetasol propionate ophthalmic nanosuspension exhibits substantially the same degree of anti-inflammatory activity as the positive control substance, the 0.1% fluorometholone ophthalmic solution.

(Example 11) Efficacy of Clobetasol Ophthalmic Nanosuspension for Rabbit Model of LPS-Induced Uveitis (1) Pulverization of Clobetasol Propionate In a 1.0 L water-cooled vertical kneader (manufactured by INOUE MFG., INC.), 50 g of clobetasol propionate (FARMABIOS S.p.A.), 550 g of sodium chloride (Tomita Salt K-30, Tomita Pharmaceutical Co., Ltd.), 4 g of anhydrous citric acid (Sigma-Aldrich Co. LLC.), and 50 g of hydrogenated soybean lecithin (Phospholipon 90H, Lipoid GmbH) were added, and were homogeneously mixed. To the mixture, 70 g of glycerin (Sigma-Aldrich Co. LLC.) was added with keeping the mixture in form of dough, and pulverized at 5° C. for 5 hours. The resulting pulverized-kneaded product (dough) was dispersed using a dispersant to give a suspension in the same manner as Example 1(1), and the particle size distribution of the clobetasol propionate was measured. The particle size distributions of clobetasol propionate were found to have the mean particle diameter (Dv) of 132 nm, the 10% particle diameter (D10) of 67 nm, the median particle diameter (D50) of 110 nm, and the 90% particle diameter (D90) of 184 nm.

(2) Preparation of 0.002% Clobetasol Propionate Ophthalmic Nanosuspension

Into a beaker, 0.076 g of the pulverized-kneaded product (dough) prepared in (1), 31.3 g of a 0.01% aqueous solution of Poloxamer 407, 25.0 g of a 1.0% aqueous solution of PVA, 0.217 g of sodium chloride, and 93.3 g of water for injection were weighed, and were dispersed using an ultrasonic device to give a crude dispersion. The crude dispersion was processed by a high-pressure homogenizer (L01-YH1, SANWA ENGINEERING LTD.) four times to obtain a dough dispersion. Into a beaker, 110.67 g of the dough dispersion was weighed, to which 1.85 g of a 0.1% aqueous solution of benzalkonium chloride and 36.91 g of a 1.0% aqueous solution of methyl cellulose were added. A 1 M aqueous solution of sodium citrate was then gradually added to adjust the pH to 7.0. Then, glycerin was added to adjust the osmotic pressure ratio to 1.0, and water for injection was added to give 184.6 g in a total amount of 0.002% clobetasol propionate ophthalmic nanosuspension. The composition and physical properties of the ophthalmic suspension are shown in the following tables.

Composition of Ophthalmic Suspension

| Components | Composition (%) |
| --- | --- |
| Clobetasol Propionate | 0.002 |
| Sodium Chloride | 0.11 |
| Hydrogenated Soybean Lecithin | 0.002 |
| Glycerin | 2.2 |
| Anhydrous Citric Acid | 0.0002 |
| Poloxamer 407 | 0.0013 |
| Polyvinyl Alcohol | 0.1 |
| Benzalkonium Chloride | 0.001 |
| Methyl Cellulose | 0.20 |
| Sodium Citrate | quantum sufficit |
| Water for Injection | quantum sufficit |

Physical Properties of Ophthalmic Suspension

| Measurement Items | Measured Values |
| --- | --- |
| Clobetasol Propionate Concentration (%) | 0.002 |
| Osmotic Pressure Ratio | 1.0 |
| pH | 7.0 |
| Viscosity (mPa · S) | 1.98 |

(3) Preparation of 0.01% Clobetasol Propionate Ophthalmic Nanosuspension

Into a beaker, 0.38 g of the pulverized-kneaded product (dough) prepared in (1), 62.5 g of a 0.01% aqueous solution of Poloxamer 407, 25.0 g of a 1.0% aqueous solution of PVA, and 62.5 g of water for injection were weighed, and were dispersed using an ultrasonic device to give a crude dispersion. The crude dispersion was processed by a high-pressure homogenizer (L01-YH1, SANWA ENGINEERING LTD.) four times to obtain a dough dispersion. Into a beaker, 119.44 g of the dough dispersion was weighed, to which 1.98 g of a 0.1% aqueous solution of benzalkonium chloride and 39.70 g of a 1.0% aqueous solution of methyl cellulose were added. A 1 M aqueous solution of sodium citrate was then gradually added to adjust the pH to 7.0. After that, glycerin was added to adjust the osmotic pressure ratio to 1.0, and water for injection was added to give 198.5 g in total amount of 0.01% clobetasol propionate ophthalmic nanosuspension. The composition and physical properties of the ophthalmic suspension are shown in the following tables.

Composition of Ophthalmic Suspension

| Components | Composition (%) |
| --- | --- |
| Clobetasol Propionate | 0.01 |
| Sodium Chloride | 0.12 |
| Hydrogenated Soybean Lecithin | 0.01 |
| Glycerin | 2.1 |
| Anhydrous Citric Acid | 0.0008 |
| Poloxamer 407 | 0.0025 |
| Polyvinyl Alcohol | 0.1 |
| Benzalkonium Chloride | 0.001 |
| Methyl Cellulose | 0.20 |
| Sodium Citrate | quantum sufficit |
| Water for Injection | quantum sufficit |

Physical Properties of Ophthalmic Suspension

| Measurement Items | Measured Values |
| --- | --- |
| Clobetasol Propionate Concentration (%) | 0.010 |
| Osmotic Pressure Ratio | 1.0 |
| pH | 7.0 |
| Viscosity (mPa · S) | 1.99 |

(4) Preparation of 0.05% Clobetasol Propionate Ophthalmic Nanosuspension

Into a beaker, 1.84 g of the pulverized kneaded product (dough) prepared in (1), 125.0 g of a 0.01% aqueous solution of Poloxamer 407, and 25.0 g of a 1.0% aqueous solution of PVA were weighed, and were dispersed using an ultrasonic device to give a crude dispersion. The crude dispersion was processed by a high-pressure homogenizer (L01-YH1, SANWA ENGINEERING LTD.) four times to obtain a dough dispersion. Into a beaker, 116.79 g of the dough dispersion was weighed, to which 1.92 g of a 0.1% aqueous solution of benzalkonium chloride and 38.45 g of a 1.0% aqueous solution of methyl cellulose were added. A 1 M aqueous solution of sodium citrate was then gradually added to adjust the pH to 7.0. Then, glycerin was added to adjust the osmotic pressure ratio to 1.0, and water for injection was added to give 192.3 g in total amount of 0.05% clobetasol propionate ophthalmic nanosuspension. The composition and physical properties of the ophthalmic suspension are shown in the following tables.

Composition of Ophthalmic Suspension

| Components | Composition Ratio (%) |
| --- | --- |
| Clobetasol Propionate | 0.05 |
| Sodium Chloride | 0.56 |
| Hydrogenated Soybean Lecithin | 0.05 |
| Glycerin | 0.50 |
| Anhydrous Citric Acid | 0.004 |
| Poloxamer 407 | 0.005 |
| Polyvinyl Alcohol | 0.1 |
| Benzalkonium Chloride | 0.001 |
| Methyl Cellulose | 0.20 |
| Sodium Citrate | quantum sufficit |
| Water for Injection | quantum sufficit |

Physical Properties of Ophthalmic Suspension

| Measurement Items | Measured Values |
| --- | --- |
| Clobetasol Propionate Concentration (%) | 0.048 |
| Osmotic Pressure Ratio | 1.0 |
| pH | 7.0 |
| Viscosity (mPa · S) | 1.99 |

(5) Efficacy for Rabbit Model of LPS-Induced Uveitis

Rabbits (Kbs:JW) were anesthetized by administering pentobarbital sodium (Somnopentyl) via their auricular veins, and 0.4% oxybuprocaine hydrochloride (Benoxil ophthalmic solution) was then ophthalmically administered into both eyes of the rabbits. After loss of corneal reflex, a lid speculum was attached to each rabbit, and 0.02 mL of LPS (Lipopolysaccharide, from E. Coli O55: sigma) adjusted to a concentration of 2 µg/mL was administered into the vitreous body using a syringe with a 30 G needle to cause inflammation. A control substance (saline), a positive control substance (durezol (registered trademark): 0.05% diflupredenate ophthalmic emulsion manufactured by Alcon Laboratories Inc.), and the test substance (0.05% ophthalmic suspension) prepared in (4) above were ophthalmically administered into both eyes of the rabbits using a micropipette at a dose of 50 µL, 4 hours before, 15 minutes after, 6 hours after, and 8 hours after the LPS administration. For each group, both eyes of 6 rabbits were used so as to set n=12 for each group. At 24 hours after the LPS administration, the rabbits were euthanized by excessive administration of pentobarbital sodium (Somnopentyl), and the whole amount of anterior chamber aqueous humor was collected using a syringe with a 26 G needle. The eyeballs were isolated and incised around the corneoscleral limbus, and the vitreous body was collected using a 1 mL syringe. The PGE2 concentrations in the collected samples of both anterior chamber aqueous humor and vitreous body were measured by ELISA assay (Prostaglandin E2 Express ELISA Kit: cayman).

(6) Results

FIG. 10 shows the results of the measurement of the PGE2 concentration in aqueous humor (evaluation of anterior eye segment), and FIG. 11 shows the results of the measurement of the PGE2 concentration in vitreous body (evaluation of posterior eye segment). These results demonstrated that when ophthalmically administered into the eyes of rabbits model of LPS-induced uveitis, the clobetasol propionate ophthalmic nanosuspension of the present invention exhibits the same level of anti-inflammatory action on uveitis (anterior eye segment) as the positive control, Durezol (registered trademark). Additionally, the PGE2 concentration in vitreous body was lower in the group administered the clobetasol propionate ophthalmic nanosuspension of the present invention than for the group administered Durezol (registered trademark), which demonstrated that the clobetasol propionate ophthalmic nanosuspension of the present invention exhibits higher anti-inflammatory activity on uveitis (posterior eye segment) than Durezol (registered trademark).

(Example 12) Efficacy of Clobetasol Ophthalmic Nanosuspension for Rabbit Model of Puncture-Induced Anterior Chamber Inflammation (1) Efficacy for Rabbit Model of Puncture-Induced Anterior Chamber Inflammation A control substance (saline), a positive control substance (Durezol (registered trademark)), and the test substances prepared in Examples 11(2), 11(3), and 11(4) (0.002%, 0.01%, and 0.05% ophthalmic suspensions) were administered into both eyes of rabbits (Kbs:JW) using a micropipette once at a dose of 50 μL. For each group, both eyes of 6 rabbits were used so as to set n=12 for each group. After 4 hours from the administration, 0.4% oxybuprocaine hydrochloride (Benoxil ophthalmic solution) was ophthalmically administered into both eyes of the rabbits. After loss of corneal reflex, a lid speculum was attached to each rabbit, and a syringe with a 26 G needle was inserted into the anterior chamber to collect the whole amount of anterior chamber aqueous humor and thus cause inflammation of the anterior eye segment. After 3 hours, the whole amount of anterior chamber aqueous humor was collected again using a syringe with a 26 G needle, and the protein concentration in anterior chamber aqueous humor was measured by BCA assay (Pierce™ BCA Protein Assay Kit: Thermo Fisher Scientific Inc.). The protein concentration in anterior chamber aqueous humor was measured by BCA assay also for the group (Normal) in which no anterior eye inflammation was caused by anterior chamber puncture.

(2) Results

FIG. 12 shows the results of the measurement of the protein concentration in anterior chamber aqueous humor, which demonstrated that the clobetasol propionate ophthalmic nanosuspensions (0.002%, 0.01%, and 0.05%) of the present invention exhibit the same level of anti-inflammatory action as the positive control, Durezol (registered trademark) (0.05% difluprednate) in ophthalmically administering into the eyes of rabbits model of puncture-induced anterior chamber inflammation.

(Example 13) Efficacy of Clobetasol Ophthalmic Nanosuspension for Rabbit Model of LPS-Induced Uveitis (1) Efficacy for Rabbit Model of LPS-Induced Uveitis Rabbits (Kbs:JW) were anesthetized by administering pentobarbital sodium (Somnopentyl) via their auricular veins, and 0.4% oxybuprocaine hydrochloride (Benoxil ophthalmic solution) was then ophthalmically administered into both eyes of the rabbits. After loss of corneal reflex, a lid speculum was attached to each rabbit, into the vitreous body of which 0.02 mL of LPS (Lipopolysaccharide, from $E.\ Coli$ O55: sigma) adjusted to a concentration of 2 μg/mL was administered using a syringe with a 30 G needle to cause inflammation. For 6 consecutive days from the next day of the LPS administration, a control substance (saline), a positive control substance (Durezol: 0.05% difluprednate ophthalmic emulsion manufactured by Alcon Laboratories Inc.), and the test substance (0.05% ophthalmic suspension) prepared in Example 11(4) were ophthalmically administered into both eyes of the rabbits using a micropipette at a dose of 50 μL on a b.i.d schedule (twice daily administration) in which the administration was done at 9:00 and 17:00 and on a q.i.d schedule (four-times daily administration) in which the administration was done at 9:00, 12:00, 15:00, and 18:00. For each group, both eyes of 4 or 5 rabbits were used so as to set n=8 or 10 for each group. After 24 hours from the LPS administration, the rabbits were euthanized by excessive administration of pentobarbital sodium (Somnopentyl). Their eyeballs were isolated and incised around the corneoscleral limbus, and the vitreous body was collected using a 1 mL syringe. The PGE2 concentrations in the collected samples were measured by ELISA assay (Prostaglandin E2 Express ELISA Kit: cayman).

(2) Results

FIG. 13 shows the results of the measurement of the PGE2 concentration in vitreous body (evaluation of posterior eye segment). For the case of the control substance, the PGE2 concentration in vitreous body was 345.6 pg/ml. The twice daily administration and four-times daily administration of the positive control Durezol yielded PGE2 concentrations in vitreous body of 256.35 pg/ml and 179.4 pg/ml, respectively, which means that Durezol has a trend toward improvement. The twice daily administration and four-times daily administration of the clobetasol propionate ophthalmic nanosuspension of the present invention yielded PGE2 concentrations in vitreous body of 219.2 pg/ml and 167.6 pg/ml, respectively, which means that the ophthalmic suspension exhibited higher anti-inflammatory activity than Durezol. It has been demonstrated that the clobetasol propionate ophthalmic nanosuspension of the present invention exhibits higher anti-inflammatory action than the positive control Durezol in ophthalmically administering into the eyes of rabbits model of LPS-induced uveitis on a b.i.d schedule (twice daily administration) as well as on a q.i.d schedule (four-times daily administration).

TABLE 1

| Pulverization method | | Pulverization formulation (g) | | | | Particle size distribution measured after pulverization (nm) | | | |
| --- | --- | --- | --- | --- | --- | --- | --- | --- | --- |
| | CP | Sodium chloride | Anhydrous citric acid | Hydrogenated soybean lecithin | Glycerin | Mean (Dv) | D10 | D50 | D90 |
| (1) | 10 | 110 | — | — | 17 | 285 | 135 | 231 | 433 |
| (2) | 10 | 110 | 0.8 | — | 17 | 260 | 143 | 222 | 363 |
| (3) | 10 | 110 | — | 10 | 17 | 147 | 78 | 124 | 210 |
| (4) | 10 | 110 | 0.8 | 5 | 17 | 166 | 86 | 138 | 241 |

TABLE 1-continued

| | Pulverization formulation (g) | | | | | Particle size distribution measured after pulverization (nm) | | | |
|---|---|---|---|---|---|---|---|---|---|
| Pulverization method | CP | Sodium chloride | Anhydrous citric acid | Hydrogenated soybean lecithin | Glycerin | Mean (Dv) | D10 | D50 | D90 |
| (5) | 10 | 110 | 0.8 | 10 | 17 | 101 | 56 | 87 | 141 |
| (6) | 10 | 110 | 0.8 | 20 | 17 | 144 | 71 | 121 | 214 |
| (7) | 10 | 110 | 2 | 5 | 17 | 137 | 65 | 112 | 209 |
| (8) | 10 | 110 | 2 | 10 | 17 | 129 | 70 | 112 | 179 |
| (9) | 10 | 110 | 2 | 20 | 17 | 147 | 66 | 121 | 228 |

TABLE 2

| Dispersant (Concentration) | General name | Manufacturer | Dispersion state Immediately after dispersing | After 1 day | Storage stability evaluation |
|---|---|---|---|---|---|
| HCO60 (0.1%) | Polyoxyethylene hydrogenated castor oil 60 | Nikko Chemicals | Transparent | Full precipitation | Fair |
| HCO40 (0.1%) | Polyoxyethylene hydrogenated castor oil 40 | Nikko Chemicals | Transparent | Full precipitation | Fair |
| Tween80 (0.1%) | Polysorbate 80 | Nikko Chemicals | Transparent | Full precipitation | Fair |
| Tween20 (0.1%) | Polysorbate 20 | Sigma-Aldrich | Transparent | Full precipitation | Fair |
| MYS40MV (0.1%) | Polyoxyl 40 stearate | Nikko Chemicals | Transparent | Full precipitation | Fair |
| PLONON 407P (0.1%) | Polyoxyethylene polyoxypropylene glycol | NOF CORPORATION | Transparent | Transparent | Good |
| Pluronic F68 (0.1%) | Polyoxyethylene polyoxypropylene glycol | NOF CORPORATION | Transparent | Transparent | Good |
| UNILUB 70DP-950B (0.1%) | Polyoxyethylene polyoxypropylene glycol | NOF CORPORATION | Transparent | Transparent | Good |
| Kuraray POVAL 217C (0.1%) | Polyvinyl alcohol | Kuraray | Transparent | Transparent | Good |
| Chondroitin sulfate C sodium salt (0.1%) | Sodium chondroitin sulfate | Wako Pure Chemical Industries | Turbid | Full precipitation | Poor |
| Polyvinylpyrrolidone K-25 (0.1%) | Polyvinylpyrrolidone | Wako Pure Chemical Industries | Turbid | Turbid | Poor |
| Poly(ethylene glycol) 400 (0.1%) | Poly(ethylene glycol) | KANTO CHEMICAL | Turbid | Full precipitation | Poor |
| Poly(ethylene glycol) 4000 (0.1%) | Poly(ethylene glycol) | KANTO CHEMICAL | Turbid | Full precipitation | Poor |

TABLE 3

| Thickener | General name | Manufacturer | Final concentration (%) | Visual observation (after 4 days) | Storage stability evaluation |
|---|---|---|---|---|---|
| Purified water (no addition of thickener) | — | — | 0 | Full precipitation | Poor |
| TC-5 (R) | Hydroxypropyl methylcellulose | Shin-Etsu Chemical | 0.1 | Transparent, with no precipitation | Good |

TABLE 3-continued

| Thickener | General name | Manufacturer | Final concentration (%) | Visual observation (after 4 days) | Storage stability evaluation |
|---|---|---|---|---|---|
| Metlose 60SH-50 | Hydroxypropyl methylcellulose | Shin-Etsu Chemical | 0.1 | Transparent, with no precipitation | Good |
| Kuraray POVAL 217C | Polyvinyl alcohol | Kuraray | 0.1 | Transparent, with modest precipitation | Fair |
| Chondroitin sulfate C sodium salt | Chondroitin sulfate | Wako Pure Chemical Industries | 0.1 | Full precipitation | Poor |
| Polyvinylpyrrolidone K-90 | Polyvinylpyrrolidone | Wako Pure Chemical Industries | 0.05 | Full precipitation | Poor |
| Poly(ethylene glycol) 6000 | Poly(ethylene glycol) | KANTO CHEMICAL | 0.1 | Full precipitation | Poor |
| Metlose SM-100 | Methyl cellulose | Shin-Etsu Chemical | 0.1 | Transparent, with no precipitation | Good |
| Metlose SM-15 | Methyl cellulose | Shin-Etsu Chemical | 0.1 | Transparent, with no precipitation | Good |
| HEC | Hydroxyethyl cellulose | Wako Pure Chemical Industries | 0.1 | Full precipitation | Poor |
| HIVISWAKO 104 | Carboxyvinyl polymer | Wako Pure Chemical Industries | 0.1 | Full precipitation | Poor |

TABLE 4

| Stored duration (days) | Storage temperature | |
|---|---|---|
| | Cycle (5° C.-25° C.) | 40° C. |
| 0 | Transparent | Transparent |
| 7 | Transparent | Transparent |

TABLE 5

| Eye drop sample | Drug concentration (%) | Filter name (Pore size: Pre-filter/ main filter) | Permeation amount (L/m$^2$) | Permeation ratio (%) |
|---|---|---|---|---|
| (1) | 0.05 | Optiscale25 (0.5/0.22) | 644 | 95.5 |
| | | Optiscale25 Capsule (0.2/0.22) | 501 | 93.0 |
| (2) | 0.05 | Optiscale25 (0.5/0.22) | 450 | 70.8 |
| | | Optiscale25 Capsule (0.2/0.22) | 659 | 72.2 |
| (3) | 0.05 | Optiscale25 (0.5/0.22) | 259 | 87.4 |
| | | Optiscale25 Capsule (0.2/0.22) | 347 | 89.1 |

TABLE 6

| Component | Composition (mg/mL) | | |
|---|---|---|---|
| | (1) | (2) | (3) |
| Clobetasol propionate | 0.5 | 0.5 | 0.5 |
| Sodium chloride | 5.5 | 5.5 | 5.9 |
| Hydrogenated soybean lecithin | 0.5 | — | — |
| Glycerin | 0.86 | 0.86 | 0.5 |
| Anhydrous citric acid | 0.04 | 0.04 | 0.04 |
| PVA | 1 | 1 | 1 |
| POE·POP glycol | 0.05 | 0.05 | — |
| BAC | 0.01 | 0.01 | 0.01 |
| HPMC | 3 | 3 | 3 |
| Sodium citrate | quantum sufficit | quantum sufficit | quantum sufficit |
| Water for injection | quantum sufficit | quantum sufficit. | quantum sufficit |

TABLE 7

| | Concentration (ng/mL) | | | | | |
|---|---|---|---|---|---|---|
| | 0.05% ophthalmic nanosuspension (mean particle diameter = 600 nm) | | 0.05% ophthalmic nanosuspension (mean particle diameter = 300 nm) | | 0.05% ophthalmic nanosuspension (mean particle diameter = 100 nm) | |
| Time (min) | Mean | SD | Mean | SD | Mean | SD |
| 15 | 0 | 0 | 14.00 | 1.07 | 23.19 | 20.61 |
| 30 | 9.27 | 2.67 | 24.45 | 13.76 | 39.92 | 7.65 |
| 60 | 6.45 | 1.24 | 25.92 | 6.51 | 75.32 | 29.8 |
| 90 | 5.45 | 1.62 | 20.80 | 8.20 | 23.19 | 1.04 |

TABLE 8

| | Concentration (ng/mL) | | | | | |
|---|---|---|---|---|---|---|
| | 0.05% ophthalmic nanosuspension (mean particle diameter = 600 nm) | | 0.05% ophthalmic nanosuspension (mean particle diameter = 300 nm) | | 0.05% ophthalmic nanosuspension (mean particle diameter = 100 nm) | |
| Time (min) | Mean | SD | Mean | SD | Mean | SD |
| 15 | 255 | 74.5 | 703.4 | 148.7 | 1210 | 391 |
| 30 | 149.1 | 140 | 640.0 | 793.3 | 203.4 | 34.3 |
| 60 | 73.34 | 24.01 | 88.98 | 32.6 | 429.4 | 68.4 |
| 90 | 5.32 | 9.22 | 78.25 | 43.99 | 95.96 | 20.34 |

TABLE 9

| | Composition (mg/mL) | | | |
|---|---|---|---|---|
| Example 7 | (1) | (2) | (3) | (4) |
| Ophthalmic nanosuspension | P | Q | R | S |
| Clobetasol propionate | 0.5 | 0.5 | 0.5 | 0.5 |
| Sodium chloride | 5.5 | 5.5 | 5.5 | 5.5 |
| Hydrogenated soybean lecithin | 0.5 | 0.5 | 0.5 | 0.5 |
| Glycerin | 0.84 | 0.84 | 0.84 | 0.84 |
| Anhydrous citric acid | 0.04 | 0.04 | 0.04 | 0.04 |
| PVA | 1 | 1 | 1 | 1 |
| POE•POP glycol | 0.05 | 0.05 | 0.05 | 0.05 |
| BAC | 0.01 | 0.01 | 0.01 | 0.01 |
| HPMC (60SH-50) | 3 | — | — | — |
| HPMC (60SH-4000) | — | 1.5 | — | — |
| MC (SM-100) | — | — | 2 | — |
| MC (SM-4000) | — | — | — | 1.5 |
| Sodium citrate | quantum sufficit | quantum sufficit | quantum sufficit | quantum sufficit |
| Water for injection | quantum sufficit | quantum sufficit | quantum sufficit | quantum sufficit |

TABLE 10

| | Concentration (ng/mL) | | | | | | | |
|---|---|---|---|---|---|---|---|---|
| | 0.05% ophthalmic nanosuspension P | | 0.05% ophthalmic nanosuspension Q | | 0.05% ophthalmic nanosuspension R | | 0.05% ophthalmic nanosuspension S | |
| Time (min) | Mean | SD | Mean | SD | Mean | SD | Mean | SD |
| 15 | 25.77 | 8.94 | 24.83 | 11.92 | 17.03 | 2.16 | 23.49 | 1.43 |
| 30 | 63.88 | 12.87 | 74.62 | 5.81 | 54.74 | 12.37 | 63.16 | 2.18 |
| 60 | 48.58 | 27.62 | 53.09 | 15.86 | 52.69 | 10.34 | 52.08 | 17.4 |
| 90 | 36.67 | 11.72 | 54.23 | 38.82 | 33.8 | 13.71 | 59.34 | 28.99 |

TABLE 11

| | Concentration (ng/mL) | | | | | | | |
|---|---|---|---|---|---|---|---|---|
| | 0.05% ophthalmic nanosuspension P | | 0.05% ophthalmic nanosuspension Q | | 0.05% ophthalmic nanosuspension R | | 0.05% ophthalmic nanosuspension S | |
| Time (min) | Mean | SD | Mean | SD | Mean | SD | Mean | SD |
| 15 | 971.9 | 162.8 | 1455.00 | 641.00 | 659.10 | 174.50 | 2141 | 708 |
| 30 | 608.40 | 228.10 | 525.70 | 5.10 | 367.7 | 37.20 | 497.3 | 59.6 |
| 60 | 260.90 | 182.30 | 204.80 | 42.90 | 269.9 | 101.90 | 177.2 | 86.4 |
| 90 | 127.00 | 36.80 | 288.20 | 198.10 | 199.9 | 88.10 | 148.4 | 48 |

What is claimed is:

1. An aqueous suspension comprising:
   nanoparticles of a glucocorticosteroid compound;
   a physiologically acceptable salt;
   glycerin;
   hydrogenated soybean lecithin; and
   anhydrous citric acid;
   wherein a mean particle diameter of the nanoparticles is 300 nm or less and a D90 particle diameter of the nanoparticles is 450 nm or less.

2. An aqueous suspension comprising nanoparticles of a glucocorticosteroid compound, wherein a mean particle diameter of the nanoparticles is 300 nm or less and a D90 particle diameter of the nanoparticles is 450 nm or less, and the nanoparticles are produced by mixing the glucocorticosteroid compound, a physiologically acceptable salt, glycerin, hydrogenated soybean lecithin and anhydrous citric acid.

3. The aqueous suspension of claim 1, wherein the glucocorticosteroid compound is one or more substances selected from the group consisting of clobetasol propionate, diflorasone diacetate, dexamethasone propionate, difluprednate, mometasone furoate, diflucortolone valerate, betamethasone butyrate propionate, fluocinonide, hydrocortisone butyrate propionate, beclomethasone dipropionate, deprodone propionate, betamethasone valerate, dexamethasone valerate, prednisolone valerate acetate, fluocinolone acetonide, hydrocortisone butyrate, clobetasone butyrate, alclometasone dipropionate, triamcinolone acetonide, flumethasone pivalate, prednisolone and hydrocortisone.

4. The aqueous suspension of claim 1, further comprising a dispersion stabilizer.

5. The aqueous suspension of claim 4, wherein the dispersion stabilizer is polyoxyethylene polyoxypropylene glycol and/or polyvinyl alcohol.

6. The aqueous suspension of claim 1, further comprising a viscosity modifier.

7. The aqueous suspension of claim 6, wherein the viscosity modifier is one or more substances selected from the group consisting of methyl cellulose, hydroxypropyl methylcellulose and polyvinyl alcohol.

8. The aqueous suspension of claim 6, comprising 1 to 10 mg/mL of the viscosity modifier.

9. A pharmaceutical composition comprising the aqueous suspension of claim 1.

10. The pharmaceutical composition of claim 9, for parenteral administration.

11. The pharmaceutical composition of claim 10, which is for an injection or for a topical preparation.

12. The pharmaceutical composition of claim 11, which is for a topical preparation for an eye, an ear, a nose or a lung.

13. The pharmaceutical composition of claim 12, which is an eye drop, an ear drop, a nose drop, or an inhaler.

14. A kit for preparing the pharmaceutical composition of claim 9, comprising nanoparticles of a glucocorticosteroid compound.

15. A method for manufacturing the pharmaceutical composition of claim 9, comprising mixing the glucocorticosteroid compound, the physiologically acceptable salt, the glycerin, the hydrogenated soybean lecithin and the anhydrous citric acid.

16. The method for manufacturing of claim 15, comprising mixing the glucocorticosteroid compound, the physiologically acceptable salt, the glycerin, the anhydrous citric acid the hydrogenated soybean lecithin, a physiologically acceptable polyol and/or water, and a dispersion stabilizer.

* * * * *